(12) United States Patent
Wong et al.

(10) Patent No.: US 8,048,856 B1
(45) Date of Patent: *Nov. 1, 2011

(54) TREATMENT METHODS USING A HEAT STABLE OXYGEN CARRIER-CONTAINING PHARMACEUTICAL COMPOSITION

(75) Inventors: Bing Lou Wong, Irvine, CA (US); Sui Yi Kwok, Hong Kong (HK); Sze Hang Lau, Hong Kong (HK)

(73) Assignee: Billion King, Ltd., Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,590

(22) Filed: Jul. 11, 2011

Related U.S. Application Data

(63) Continuation-in-part of application No. 13/013,850, filed on Jan. 26, 2011, which is a continuation-in-part of application No. 12/957,430, filed on Dec. 1, 2010, now Pat. No. 7,932,356, which is a continuation-in-part of application No. 12/821,214, filed on Jun. 23, 2010.

(51) Int. Cl.
A61K 38/42 (2006.01)

(52) U.S. Cl. .................. 514/13.4; 514/13.5; 514/19.2; 530/385

(58) Field of Classification Search .................. None
See application file for complete search history.

(56) References Cited

U.S. PATENT DOCUMENTS

| | | |
|---|---|---|
| 4,543,209 A | 9/1985 | Tayot et al. |
| 4,598,064 A | 7/1986 | Walder |
| 4,600,531 A | 7/1986 | Walder |
| 4,831,012 A | 5/1989 | Estep |
| 4,987,048 A | 1/1991 | Shinozaki et al. |
| 5,084,558 A | 1/1992 | Rausch et al. |
| 5,189,146 A | 2/1993 | Hsia |
| RE34,271 E | 6/1993 | Walder |
| 5,296,465 A | 3/1994 | Rausch et al. |
| 5,344,393 A | 9/1994 | Roth et al. |
| 5,439,882 A | 8/1995 | Feola et al. |
| 5,451,205 A | 9/1995 | Roth et al. |
| 5,591,710 A | 1/1997 | Hsia |
| 5,618,919 A | 4/1997 | Rausch et al. |
| 5,631,219 A | 5/1997 | Rosenthal et al. |
| 5,691,453 A | 11/1997 | Wertz et al. |
| 5,725,839 A | 3/1998 | Hsia |
| 5,741,893 A | 4/1998 | Hsia |
| 5,753,616 A | 5/1998 | Rausch et al. |
| 5,767,089 A | 6/1998 | Hsia |
| 5,789,376 A | 8/1998 | Hsia |
| 5,804,561 A | 9/1998 | Hsia |
| 5,807,831 A | 9/1998 | Hsia |
| 5,811,005 A | 9/1998 | Hsia |
| 5,814,601 A | 9/1998 | Winslow et al. |
| 5,817,528 A | 10/1998 | Bohm et al. |
| 5,817,632 A | 10/1998 | Hsia |
| 5,824,781 A | 10/1998 | Hsia |
| 5,840,701 A | 11/1998 | Hsia |
| 5,840,851 A | 11/1998 | Plomer et al. |
| 5,865,784 A | 2/1999 | Faithfull et al. |
| 5,895,810 A | 4/1999 | Light et al. |
| 5,905,141 A | 5/1999 | Rausch et al. |
| 5,955,581 A | 9/1999 | Rausch et al. |
| 6,007,774 A | 12/1999 | Faithfull et al. |
| 6,054,427 A | 4/2000 | Winslow |
| 6,127,043 A | 10/2000 | Lange |
| 6,160,098 A | 12/2000 | Kerwin |
| 6,242,417 B1 | 6/2001 | Gerber et al. |
| 6,270,952 B1 | 8/2001 | Cook et al. |
| 6,288,027 B1 | 9/2001 | Gawryl et al. |
| 6,323,175 B1 | 11/2001 | Hsia |
| 6,399,357 B1 | 6/2002 | Winge |
| 6,432,918 B1 | 8/2002 | Winslow |
| 6,486,306 B1 | 11/2002 | Winge |
| 6,506,725 B1 | 1/2003 | Rausch et al. |
| RE38,081 E | 4/2003 | Faithfull et al. |
| 6,566,504 B2 | 5/2003 | Bhattacharya et al. |
| 6,599,878 B2 | 7/2003 | Rooney |
| 6,610,832 B1 | 8/2003 | Gawryl et al. |
| 6,709,810 B2 | 3/2004 | Cook et al. |
| 6,740,139 B2 | 5/2004 | Russell et al. |
| 6,747,132 B2 | 6/2004 | Privalle et al. |
| 6,844,317 B2 | 1/2005 | Winslow et al. |
| 6,894,150 B1 | 5/2005 | Tye |
| 7,038,016 B2 | 5/2006 | Talarico et al. |
| 7,101,846 B2 | 9/2006 | Winslow |
| 7,293,985 B2 | 11/2007 | Cook et al. |

(Continued)

OTHER PUBLICATIONS

Napolitano L.M., "Hemoglobin-based oxygen carriers: first, second or third generation? Human or bovine? Where are we now?", Crit Care Clin. 25, 279-301 (2009).

(Continued)

*Primary Examiner* — Christina Bradley
(74) *Attorney, Agent, or Firm* — Ella Cheong Hong Kong; Margaret Burke; Sam Yip

(57) ABSTRACT

A highly purified and heat stable cross-linked nonpolymeric tetrameric hemoglobin suitable for use in mammals without causing renal injury and vasoconstriction is provided. A high temperature and short time (HTST) heat processing step is performed to remove undesired dimeric form of hemoglobin, uncross-linked tetrameric hemoglobin, and plasma protein impurities effectively. Addition of N-acetyl cysteine after heat treatment and optionally before heat treatment maintains a low level of met-hemoglobin. The heat stable cross-linked tetrameric hemoglobin can improve and prolong oxygenation in normal and hypoxic tissue. In another aspect, the product is used in the treatment of various types of cancer such as leukemia, colorectal cancer, lung cancer, breast cancer, liver cancer, nasopharyngeal carcinoma and esophageal cancer. The inventive hemoglobin can also be used to prevent tumor metastasis and recurrence following surgical tumor excision. Further the inventive tetrameric hemoglobin can be administered to patients prior to chemotherapy and radiation treatment.

7 Claims, 19 Drawing Sheets

(2 of 19 Drawing Sheet(s) Filed in Color)

U.S. PATENT DOCUMENTS

| | | |
|---|---|---|
| 7,411,044 B2 | 8/2008 | Avella et al. |
| 7,494,974 B2 | 2/2009 | Tye |
| 7,501,499 B2 | 3/2009 | Acharya et al. |
| 7,504,377 B2 | 3/2009 | Tye |
| 7,625,862 B2 | 12/2009 | Winslow et al. |
| 7,655,392 B2 | 2/2010 | Stassinopoulos |
| 7,759,306 B2 | 7/2010 | Simoni et al. |
| 7,932,356 B1 | 4/2011 | Wong et al. |
| 2010/0209532 A1 | 8/2010 | Dube et al. |
| 2011/0129908 A1 | 6/2011 | Owen et al. |

OTHER PUBLICATIONS

Jiin-Yu Chen et al., "A review of blood substitutes; examining the history, clinical trial results, and ethics of hemoglobin-based oxygen carriers", Clinics 64(8), 803-813 (2009).

Larny ML et al., "Randomized Trial of Dlaspirin Cross-linked Hemoglobin Solution as an Alternative to Blood Transfusion after Cardiac Surgery", Anesthesiology 92(3), 646-656 (2000).

Lois R. Manning et al., "Subunit dissociations in natural and recombinant hemoglobins", Protein Science 5(4), 775-781 (1996).

Ronald Kluger et al., "Protein-protein coupling and its application to functional red cell substitutes", Chem Commun (Camb). 46(8), 1194-1202 (2010).

Ronald Kluger, "Red cell substitutes from hemoglobin-do we start all over again?", Current Opinion in Chemical Biology 14(4), 538-543 (2010).

Kenji Sampei et al., "Role of nitric oxide scavenging in vascular response to cell-free hemoglobin transfusion", Am J Physiol Heart Circ Physiol 289(3), H1191-H1201 (2005).

Tao Hu et al., "Preparation and characterization of dimeric bovine hemoglobin tetramers", Journal of Protein Chemistry 22(5), 411-416(2003).

Tao Hu et al., "PEGylation of Val-1(alpha) destabilizes the tetrameric structure of hemoglobin", Biochemistry 48(3), 608-616 (2009).

Kim D Vandegriff et al., "Hemospan: design principles for a new class of oxygen therapeutic", Artificial organs 33(2), 133-138 (2009).

Thoralf Kerner of al., "DCL-Hb for trauma patients with severe hemorrhagic shock; the European "On-Scene" multicenter study", Intensive Care Medicine 29(3), 378-386 (2003).

Chad R. Haney et al., "Purification and chemical modifications of hemoglobin in developing hemoglobin based oxygen carriers", Advanced Drug Delivery Reviews 40(3), 153-169 (2000).

Donat R. Spahn et al., "Artificial O2 carriers : Status in 2005", Current pharmaceutical design 11(31), 4099-4114 (2005).

Andre F. Palmer et al., "Tangential flow filtration of hemoglobin", Biotechnol Prog. 25(1), 189-199 (2009).

David C. Irwin et al., "Polymerized bovine hemoglobin decreases oxygen delivery during normoxia and acute hypoxia in the rat", Am J Physiol Heart Circ Physiol 295(3), H1090-H1099 (2008).

Guoyong Sun et al, "Preparation of Ultrapure Bovine and Human Hemoglobin by Anion Exchange Chromatography", J Chromatogr B Analyt Technol Biomed Life Sci. 867(1), 1-7 (2008).

Yiping Jia et al., "Effects of cross-linking end zero-link polymerization on oxygen transport and redox chemistry of bovine hemoglobin", Biochimica et Biophysica Acta 1794(8), 1234-1242 (2009).

Cai Jin et al., "Chemically Modified Porcine Hemoglobins and Their Biological Properties", Protein and Peptide Letters, vol. 11, No. 4, 353-360 (2004).

U.S. Appl. No. 12/821,214, Wong et al.

Ameri K et al., (2010) Circulating tumour cells demonstrate an altered response to hypoxia and an aggressive phenotype. Br J Cancer; 102(3):561-9.

Morris Sherman. (2008) Recurrence of Hepatocellular Carcinoma. N Engl J Med; 359:2045-2047.

Van Der Bilt J. D. et al., (2005) Ischemia/reperfusion accelerates the outgrowth of hepatic micrometastases in a highly standardized murine model. Hepatology;42(1):165-75.

Ku Y. et al., (1999) Stimulation of haematogenous liver metastases by ischaemia-reperfusion in rats. Eur J Surg.; 165(8):801-7.

Yu et al., Cancer Treatment Reviews (2007) 33, pp. 757-761.

U.S. Appl. No. 13/013,850, Wong et al.

U.S. Appl. No. 13/083,639, Wong et al.

U.S. Appl. No. 13/097,183, Wong et al.

Raabe et al., Strahlentherapie und Onkologie, No. 11, 2005, pp. 730-737, "No Effect of the Hemoglobin Solution HBOC-201 on the Response of the Rat R1H Tumor to Fractionated Irradiation."

Teicher (I) et al. I. J. Radiation Oncology, vol. 21, No. 4, pp. 969-975 1998, "Effect of Oxygen Level on the Enhancement of Tumor Response to Radiation by Perfluorochemical Emulsions of a Bovine Hemoglobin Preparation".

Teicher (II) et al., In Vivo, 9: 11-18 (1995), "Increased Efficacy of Chemo- and Radio-therapy by a Hemoglobin Solution in the 9L Gliosarcoma".

Lindberg et al., In Vivo, 12: 167-174 (1998).

Man et al., Liver Transplantation, vol. 13, (2007) pp. 1669-1677.

Ozaki et al., Liver Transplantation, vol. 13, (2007) pp. 1623-1626.

Title for Ozaki et al. is "Surgical Stress and Tumor Behavior: Impact of Ischemia-Reperfusion and Hepatic Resection on Tumor Progression".

Title for Lindberg et al. is "Increased Tissue Oxygenation and Enhanced Radiation Sensitivity of Solid Tumors in Rodents Following Polyethylene Glycol Conjugated Bovine Hemoglobin Administration".

Title for Man et al. is Ischemia-Reperfusion of Small Liver Remnant Promotes Liver Tumor Growth and Metastases-Activation of Cell Invasion and Migration Pathways.

Alpha hemoglobin chain

```
B  -VLSAADKGNVKAAWGKVGGHAAEYGAEALERMFLSFPTTKTYFPHFDLSHGSAQVKGHGAKVAAALTKAVEHLDDLPGA   79
H  MVLSPADKTNVKAAWGKVGAHAGEYGAEALERMFLSFPTTKTYFPHFDLSHGSAQVKGHGKKVADALTNAVAHVDDMPNA   80
C  -VLSPADKTNIKSTWDKIGGHAGDYGGEALDRTFQSFPTTKTYFPHFDLSPGSAQVKAHGKKVADALTTAVAHLDDLPGA   79
P  -VLSAADKADVKAAYGKVGAHAGEAGAEALERMFLGFTTTKTYFPHFDLSHGSDEVKAHGEKVADALTKAVGHLDDMPGA   79
E  MVLSAADKTNVKAAWSKVGGHAGEFGAEALERMFLGFPTTKTYFPHFDLSHGSAQVKAHGKKVGDALTLAVGHLDDLPGA   80

B  LSELSDLHAHKLRVDPVNFKLLSHSLLVTLASHLPSDFTPAVHASLDKFLANVSTVLTSKYR   141
H  LSALSDLHAHKLRVDPVNFKLLSHCLLVTLAAHLPAEFTPAVHASLDKFLASVSTVLTSKYR   142
C  LSALSDLHAYKLRVDPVNFKLLSHCLLVTLACHHPTEFTPAVHASLDKFFAAVSTVLTSKYR   141
P  LSALSDLHAIKLRVDPVDFKLLSHCLLSTLAVHLPDDFTPAVHADLDKFLADVSTVLDSKYR   141
E  LSNLSDLHAHKLRVDPVNFKLLSHCLLSTLAVHLPNDFTPAVHASLDKFLSSVSTVLTSKYR   142
```

Beta hemoglobin chain

```
B  M--LTAEEKAAVTAFWGKVKVDEVGGEALGRLLVVYPWTQRFFESFGDLSTADAVMNNPKVKAHGKKVLDSFSNGMKHLD   78
H  MVHLTPEEKSAVTALWGKVNVDEVGGEALGRLLVVYPWTQRFFESFGDLSTPDAVMGNPKVKAHGKKVLGAFSDGLAHLD   80
P  MVHLSAEEKEAVLGLWGKVNVDEVGGEALGRLLVVYPWTQRFFESFGDLSNADAVMGNPKVKAHGKKVLQSFSDGLKHLD   80
E  MVQLSGEEKAAVLALWDKVNEEEVGGEALGRLLVVYPWTQRFFDSFGDLSNPGAVMGNPKVKAHGKKVLHSFGEGVHHLD   80

B  DLKGTFAALSELHCDKLHVDPENFKLLGNVLVVVLARNFGKEFTPVLQADFQKVVAGVANALAHRYH   145
H  NLKGTFATLSELHCDKLHVDPENFRLLGNVLVCVLAHHFGKEFTPPVQAAYQKVVAGVANALAHKYH   147
P  NLKGTFAKLSELHCDQLHVDPENFRLLGNVIVVVLARRLGHDFNPNVQAAFQKVVAGVANALAHKYH   147
E  NLKGTFAALSELHCDKLHVDPENFRLLGNVLVVVLARHFGKDFTPELQASYQKVVAGVANALAHKYH   147
```

FIG. 1

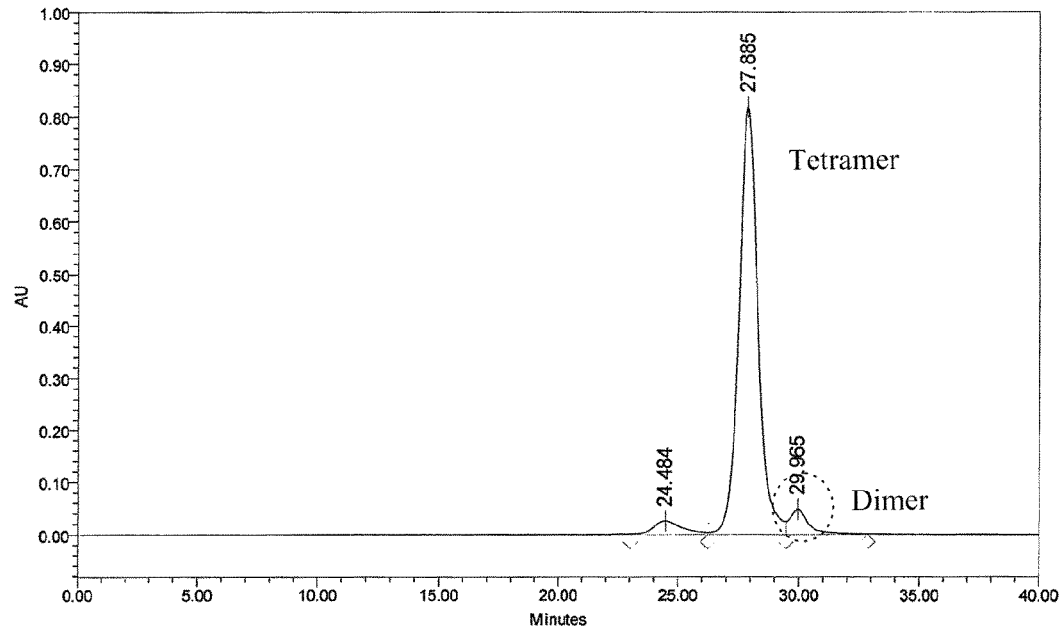
(a) No heat treatment
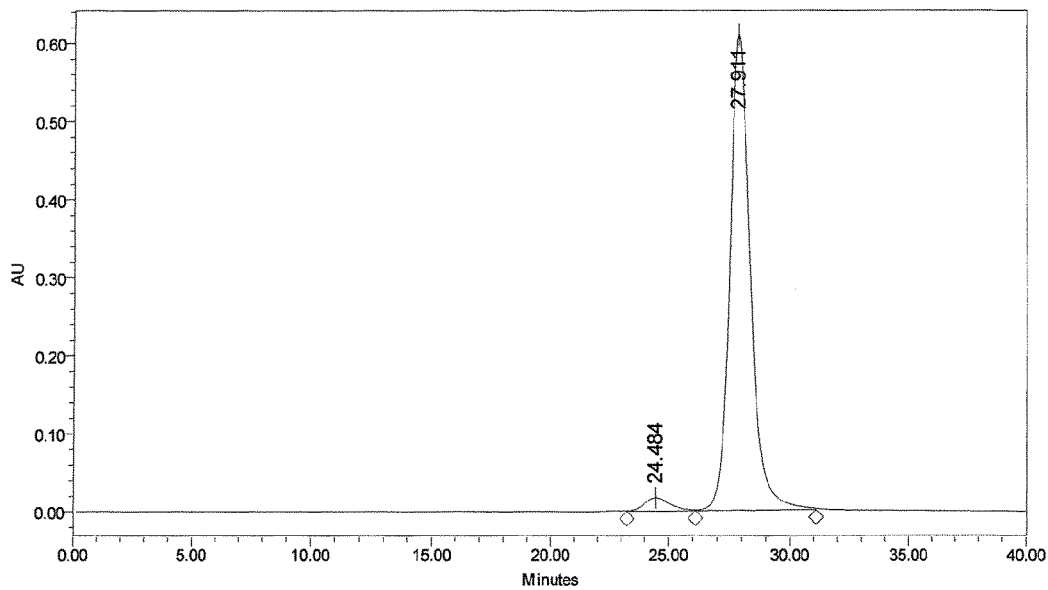
(b) Heat-treated (90°C for 45 sec - 2 min or 80°C for 30 min), stabilized cross-linked tetrameric hemoglobin
FIG. 4

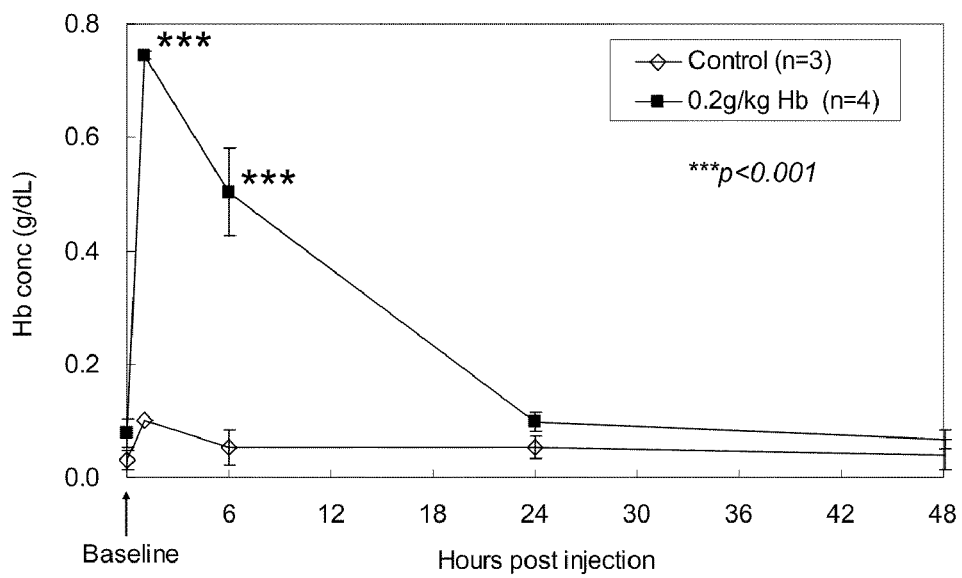
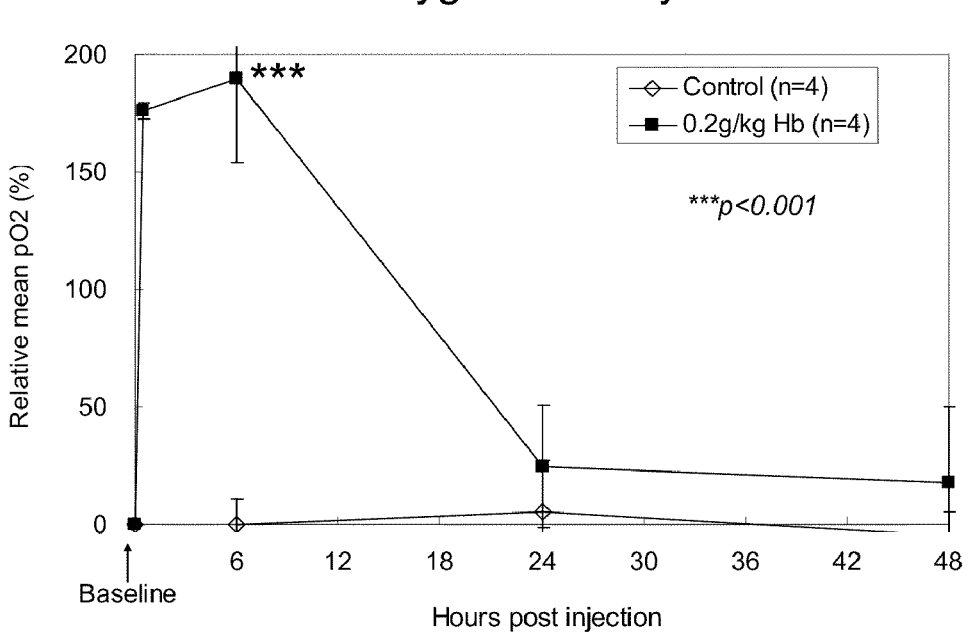
FIG. 7

A
Nasopharyngeal Cancer
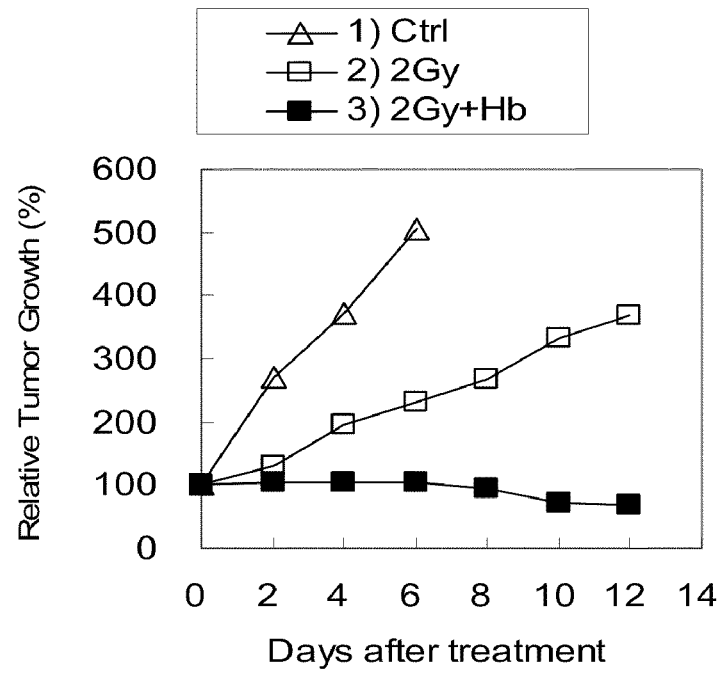
B
Liver Cancer
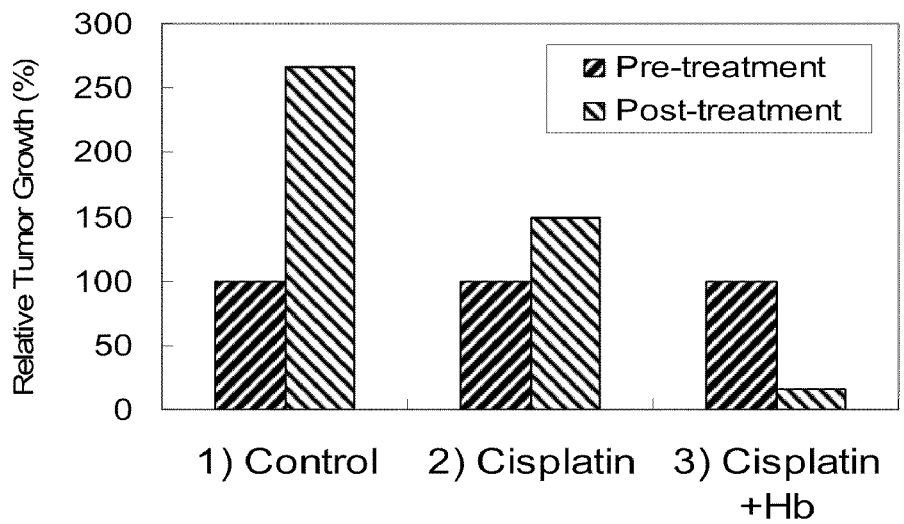
FIG. 9

*Hb= heat stable cross-linked tetrameric hemoglobin

TREATMENT METHODS USING A HEAT STABLE OXYGEN CARRIER-CONTAINING PHARMACEUTICAL COMPOSITION

CROSS-REFERENCE TO RELATED APPLICATIONS

This application is a continuation-in-part of U.S. application Ser. No. 13/013,850, filed Jan. 25, 2011, which is a continuation-in-part of U.S. application Ser. No. 12/957,430 (now U.S. Pat. No. 7,932,356), filed Dec. 1, 2010, which is a continuation-in-part of U.S. application Ser. No. 12/821,214, filed Jun. 23, 2010.

The patent or application file contains at least one drawing executed in color. Copies of this patent or patent application publication with color drawing(s) will be provided by the Office upon request and payment of the necessary fee.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright © 2010, Billion King International Limited, All Rights Reserved.

TECHNICAL FIELD

The present invention relates to a method for the preparation of a heat stable oxygen-carrier-containing pharmaceutical composition and the composition made by the process. The present invention also relates to the use of the heat stable oxygen carrier-containing pharmaceutical composition for cancer treatment, oxygen-deprivation disorders and organ preservation for humans and other animals.

BACKGROUND OF INVENTION

Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Since hemoglobin has this oxygen transport feature, it can be used as a potent oxygen supplier if it can be stabilized ex vivo and used in vivo.

Naturally-occurring hemoglobin is a tetramer which is generally stable when present within red blood cells. However, when naturally-occurring hemoglobin is removed from red blood cells, it becomes unstable in plasma and splits into two $\alpha$-$\beta$ dimers. Each of these dimers is approximately 32 kDa in molecular weight. These dimers may cause substantial renal injury when filtered through the kidneys and excreted. The breakdown of the tetramer linkage also negatively impacts the sustainability of the functional hemoglobin in circulation.

In order to solve the problem, recent developments in hemoglobin processing have incorporated various cross-linking techniques to create intramolecular bonds within the tetramer as well as intermolecular bonds between the tetramers to form polymeric hemoglobin. The prior art teaches that polymeric hemoglobin is the preferred form in order to increase circulatory half-life of the hemoglobin. However, as determined by the present inventors, polymeric hemoglobin more readily converts to met-hemoglobin in blood circulation. Met-hemoglobin cannot bind oxygen and therefore cannot oxygenate tissue. Therefore, the cross-linking taught by the prior art that causes the formation of polymeric hemoglobin is a problem. There is a need in the art for a technique that permits intramolecular crosslinking to create stable tetramers without the simultaneous formation of polymeric hemoglobin.

Further problems with the prior art attempts to stabilize hemoglobin include production of tetrameric hemoglobin that includes an unacceptably high percentage of dimer units; the presence of dimers makes the hemoglobin composition unsatisfactory for administration to mammals. The dimeric form of the hemoglobin can cause severe renal injury in a mammalian body; this renal injury can be severe enough to cause death. Therefore, there is a need in the art to create stable tetrameric hemoglobin with undetectable dimeric form in the final product.

Another problem with prior art hemoglobin products is a sudden increase in blood pressure following administration. In the past, vasoconstriction events have been recorded from older generation of hemoglobin based oxygen carriers. For instance, the Hemopure® product (Biopure Co., USA) resulted in higher mean arterial pressure (124±9 mmHg) or 30% higher when compared to the baseline (96±10 mmHg) as disclosed by Katz et al., 2010. Prior attempts to solve this problem have relied on sulfhydryl reagents to react with hemoglobin sulfhydryl groups, allegedly to prevent endothelium-derived relaxing factor from binding to the sulfhydryl groups. However, the use of sulfhydryl treatment adds processing steps, resulting in added cost and impurities which must be later removed from the hemoglobin composition. Thus there is a need in the art for a process to prepare hemoglobin which will not cause vasoconstriction and high blood pressure when applied to a mammal.

Further problems with prior art attempts to create stable hemoglobin include the presence of protein impurities such as immunoglobin G that can cause allergic effects in mammals. Therefore, there is a need in the art for a process which can produce stable tetrameric hemoglobin without protein impurities.

In addition to the above problems, there is a need in the art for a stabilized tetrameric hemoglobin that is dimer free, phospholipid free and capable of production on an industrial scale.

SUMMARY OF INVENTION

The present invention provides a method for processing a nonpolymeric, heat stable purified cross-linked tetrameric hemoglobin suitable for use in mammals without causing severe renal injury, vascular detrimental effects and severe adverse events including death. The present invention removes the dimeric form of hemoglobin, uncross-linked tetrameric hemoglobin, phospholipids and protein impurities. Additionally, the present invention uses (1) an instant cytolysis apparatus for precise and controlled hypotonic lysis, (2) a flowthrough column chromatography, (3) a high temperature short time (HTST) apparatus for heat processing the hemoglobin solution in the purification process to remove the undesirable non-stabilized dimers of hemoglobin and to remove the protein impurities, for example immunoglobin-G, so that renal injury, vascular detrimental effects and other toxicity reactions can be avoided, and (4) an air-tight infusion bag packaging to avoid oxygen intrusion into the product.

The method includes a starting material of mammalian whole blood including at least red blood cells and plasma. Red blood cells are separated from the plasma in the mammalian whole blood followed by filtering to obtain a filtered red blood cell fraction. The filtered red blood cell fraction is washed to remove plasma protein impurities. The washed red blood cells are disrupted by a controlled hypotonic lysis for a time sufficient to lyse red blood cells without lysing white blood cells in an instant cytolysis apparatus at a flow rate of 50-1000 liters/hr. Filtration is performed to remove at least a portion of the waste retentate from the lysate. A first hemoglobin solution is extracted from the lysate.

A first ultrafiltration process is performed using an ultrafiltration filter configured to remove impurities having a higher molecular weight than tetrameric hemoglobin and to further remove any viruses and residual waste retentate from the first hemoglobin solution to obtain a second hemoglobin solution. Flowthrough column chromatography is performed on the second hemoglobin solution to remove protein impurities, dimeric hemoglobin and phospholipids to form a phospholipid-free hemoglobin solution. A second ultrafiltration process is performed on the phospholipid-free hemoglobin solution using a filter configured to remove impurities resulting in a concentrated purified phospholipid-free hemoglobin solution.

At least a portion of the α-α subunits of the purified hemoglobin are cross-linked by bis-3,5-dibromosalicyl fumarate to form heat stable cross-linked hemoglobin without the formation of polymeric hemoglobin such that the molecular weight of the resultant nonpolymeric cross-linked tetrameric hemoglobin is 60-70 kDa. The expression "nonpolymeric" as used herein, refers to tetrameric hemoglobin that is not intermolecularly cross-linked with other hemoglobin molecules or any other non-hemoglobin molecules such as PEG. A suitable physiological buffer such as phosphate buffered saline (PBS), lactated Ringer's solution, acetated Ringer's solution, or Tris buffer is exchanged for the cross-linked tetrameric hemoglobin. Any residual chemicals are removed using tangential-flow filtration.

Following this procedure, the cross-linked hemoglobin is heat-treated to remove any residual non-cross-linked tetrameric hemoglobin and any non-stabilized hemoglobin, for example the dimeric form of hemoglobin, and any other protein impurities. Prior to the heat treatment N-acetyl cysteine is optionally added at a concentration of approximately 0.2% to the cross-linked tetrameric hemoglobin to prevent formation of met-hemoglobin. Immediately following heat treatment and cooling, N-acetyl cysteine is added at a concentration of approximately 0.2% to 0.4% to further prevent formation of met-hemoglobin. The heat treatment is preferably a high temperature short time treatment conducted at approximately 70° C. to 95° C. for 30 seconds to 3 hours with subsequent cooling to 25° C. Any precipitates formed during the heat treatment are removed by centrifugation or a filtration apparatus to form a clear solution thereafter.

The dimer-free, phospholipid-free, protein impurities-free, heat stable, nonpolymeric cross-linked tetrameric hemoglobin is then added to a pharmaceutically acceptable carrier.

Thereafter, the heat stable, cross-linked tetrameric hemoglobin is formulated and packaged in a custom-made and air-tight polyethylene, ethylene-vinyl-acetate, ethylene-vinyl alcohol (PE, EVA, EVOH) infusion bag. The packaging prevents oxygen contamination which results in the formation of inactive met-hemoglobin.

The heat stable cross-linked tetrameric hemoglobin produced by the above method is used for the treatment of various cancers such as leukemia, colorectal cancer, lung cancer, breast cancer, liver cancer, nasopharyngeal cancer and esophageal cancer. The mechanism for destroying cancer cells is to improve oxygenation of tumors in a hypoxic condition, thereby enhancing the sensitivity towards radiation and chemotherapeutic agents. The heat stable cross-linked tetrameric hemoglobin is also used for preservation of organ tissue during transplant or for preservation of the heart in situations where there is a lack of oxygen supply in vivo, such as in an oxygen-deprived heart.

BRIEF DESCRIPTION OF THE DRAWINGS

FIG. 1 depicts the amino acid sequence alignment of different hemoglobins.

FIG. 4 depicts high performance liquid chromatography analysis for (a) non-heat treated cross-linked tetrameric hemoglobin, and (b) heat stable cross-linked tetrameric hemoglobin which has undergone a heat treatment at 90° C. for 45 seconds to 2 minutes or 80° C. for 30 minutes.

FIG. 7 shows an improvement of oxygenation in normal tissue. Injection of 0.2 g/kg heat stable cross-linked tetrameric hemoglobin solution results in a significant increase in (A) plasma hemoglobin concentration and (B) oxygen delivery to muscle.

FIG. 9 shows partial tumor shrinkage in rodent models of (A) nasopharyngeal carcinoma (NPC) and (B) liver tumor.

DETAILED DESCRIPTION OF INVENTION

Figure 2:
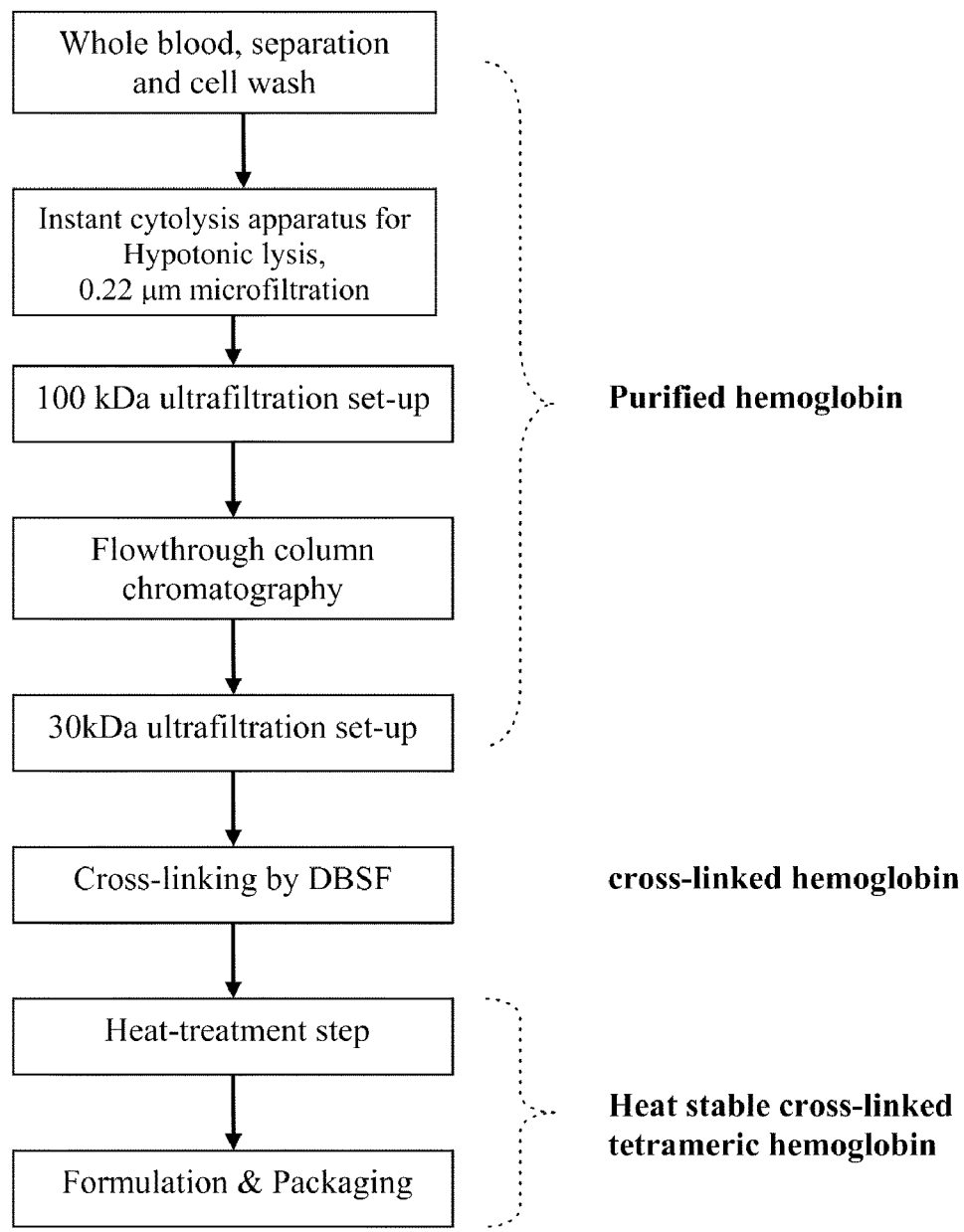
FIG. 2 is a flow-chart depicting an overview of the process of the present invention.

Hemoglobin is an iron-containing oxygen-transport protein in red blood cells of the blood of mammals and other animals. Hemoglobin exhibits characteristics of both the tertiary and quaternary structures of proteins. Most of the amino acids in hemoglobin form alpha helices connected by short non-helical segments. Hydrogen bonds stabilize the helical sections inside the hemoglobin causing attractions within the molecule thereto folding each polypeptide chain into a specific shape. A hemoglobin molecule is assembled from four globular protein subunits. Each subunit is composed of a polypeptide chain arranged into a set of α-helix structural segments connected in a "myoglobin fold" arrangement with an embedded heme group.

The heme group consists of an iron atom held in a heterocyclic ring, known as a porphyrin. The iron atom binds equally to all four nitrogen atoms in the center of the ring which lie in one plane. Oxygen is then able to bind to the iron center perpendicular to the plane of the porphyrin ring. Thus a single hemoglobin molecule has the capacity to combine with four molecules of oxygen.

In adult humans, the most common type of hemoglobin is a tetramer called hemoglobin A consisting of two α and two β non-covalently bound subunits designated as α2β2, each made of 141 and 146 amino acid residues respectively. The size and structure of α and β subunits are very similar to each other. Each subunit has a molecular weight of about 16 kDa for a total molecular weight of the tetramer of about 65 kDa. The four polypeptide chains are bound to each other by salt bridges, hydrogen bonds and hydrophobic interaction. The structure of bovine hemoglobin is similar to human hemoglobin (90.14% identity in α chain; 84.35% identity in β chain). The difference is the two sulfhydryl groups in the bovine hemoglobin positioned at β Cys 93, while the sulfhydryls in human hemoglobin are at positioned at α Cys 104, β Cys 93 and β Cys 112 respectively. FIG. 1 shows the amino acid sequences alignment of bovine, human, canine, porcine and equine hemoglobin, respectively labeled B, H, C, P, and E. The unlike amino acids from various sources are shaded. FIG. 1 indicates that human hemoglobin shares high similarity with bovine, canine, porcine and equine when comparing their amino acid sequences.

In naturally-occurring hemoglobin inside the red blood cells, the association of an α chain with its corresponding β chain is very strong and does not disassociate under physiological conditions. However, the association of one αβ dimer with another αβ dimer is fairly weak outside red blood cells. The bond has a tendency to split into two αβ dimers each approximately 32 kDa. These undesired dimers are small enough to be filtered by the kidneys and be excreted, with the result being potential renal injury and substantially decreased intravascular retention time.

Therefore, it is necessary to stabilize any hemoglobin that is used outside of red blood cells both for efficacy and safety. The process for producing the stabilized hemoglobin is outlined below; an overview of the process of the present invention is presented in the flow chart of FIG. 2.

Initially, a whole blood source is selected as a source of hemoglobin from red blood cells. Mammalian whole blood is selected including, but not limited to, human, bovine, porcine, equine, and canine whole blood. The red blood cells are separated from the plasma, filtered, and washed to remove plasma protein impurities.

Figure 3:
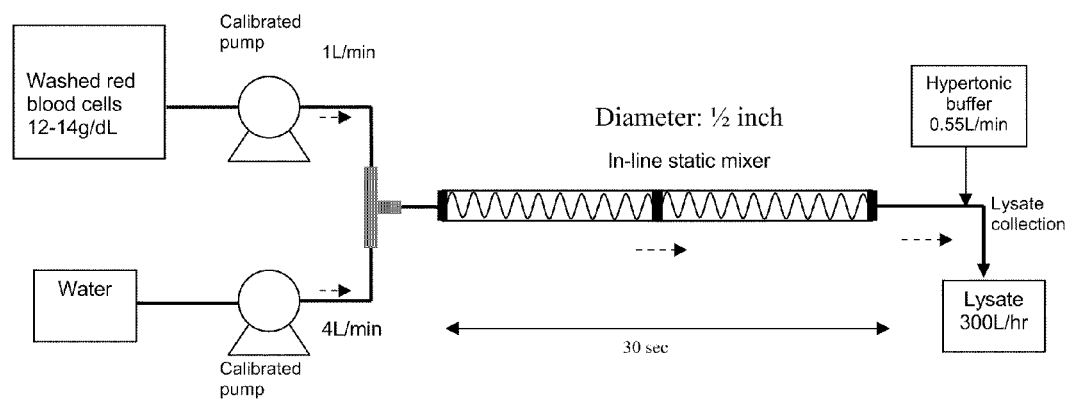
FIG. 3 schematically depicts an instant cytolysis apparatus used in the process of the present invention.

In order to release the hemoglobin from the red blood cells, the cell membrane is lysed. Although various techniques can be used to lyse red blood cells, the present invention uses lysis under hypotonic conditions in a manner which can be precisely controlled at volumes suitable for industrial-scale production. To this end, an instant cytolysis apparatus as seen in FIG. 3 is used to lyse the red blood cells. Hypotonic lysis creates a solution of lysate including hemoglobin and a waste retentate. To enable industrial-scale production, the lysis is carefully controlled such that only red blood cells are lysed without lysing white blood cells or other cells. In one embodiment, the size of the instant cytolysis apparatus is selected such that the red blood cells traverse the apparatus in 2 to 30 seconds or otherwise a time sufficient to lyse the red blood cells and preferably, 30 seconds. The instant cytolysis apparatus includes a static mixer. Deionized and distilled water is used as a hypotonic solution. Of course it is understood that the use of other hypotonic solutions having different saline concentrations would result in different time periods for red blood cell lysis. Because the controlled lysis procedure lyses the red blood cells only, not white blood cells or cellular matter, it minimizes the release of toxic proteins, phospholipids or DNA from white blood cells and other cellular matter. A hypertonic solution is added immediately after 30 seconds, that is, after the red blood-cell containing solution has traversed the static mixer portion of the instant cytolysis apparatus. The resultant hemoglobin has a higher purity and lower levels of contaminants such as undesired DNA and phospholipids than hemoglobin resulted from using other lysis techniques. Undesired nucleic acids from white blood cells and phospholipids impurities are not detected in the hemoglobin solution by polymerase chain reaction (detection limit=64 pg) and high performance liquid chromatography (HPLC, detection limit=1 µg/ml) method respectively.

Two ultrafiltration processes are performed: one which removes impurities having molecular weights greater than hemoglobin before flowthrough column chromatography, and another which removes impurities having molecular weights less than hemoglobin after flowthrough column chromatography. The latter ultrafiltration process concentrates the hemoglobin. In some embodiments, a 100 kDa filter is used for the first ultrafiltration, while a 30 kDa filter is used for the second ultrafiltration.

Flowthrough column chromatography is used to remove protein impurities in the purified hemoglobin solution such as immunoglobin-G, albumin and carbonic anhydrase. In some embodiments, column chromatography is carried out by using one or a combination of commercially available ion exchange columns such as a DEAE column, CM column, hydroxyapatite column, etc. The pH for column chromatography is typically from 6 to 8.5. In one embodiment, a flowthrough CM column chromatography step is used to remove protein impurities at pH 8.0. Enzyme-linked immunosorbent assay (ELISA) is performed to detect the protein impurities and phospholipids remaining in the sample after elution from the column chromatography. This unique flowthrough column chromatography separation enables a continuous separation scheme for industrial-scale production. The ELISA result shows that the amount of these impurities are substantially low in the eluted hemoglobin (immunoglobin-G: 44.3 ng/ml; albumin: 20.37 ng/ml; carbonic anhydrase: 81.2 µg/ml). The protein impurities removal results using different kinds of column with different pH values are shown in Table 1 below.

TABLE 1

| Column (pH condition) | Removal percentage (%) | | |
|---|---|---|---|
| | Carbonic anhydrase | Albumin | Immunoglobin-G |
| DEAE (at pH 7.5) | — | 68 | 29.8 |
| DEAE (at pH 7.8) | — | 60 | 50.9 |
| CM (at pH 6.2) | — | 32 | 21.8 |
| CM (at pH 8.0) | 5.6 | 53.2 | 66.4 |
| Hydroxyapatite (at pH 7.5) | 4.5 | 23.5 | 22.8 |

Following the column chromatographic process, the hemoglobin is subjected to cross-linking by bis-3,5-dibromosalicyl fumarate (DBSF). In order to prevent formation of polymeric hemoglobin, the reaction is carefully controlled in a deoxygenated environment (preferably less than 0.1 ppm dissolved oxygen level) with a molar ratio of hemoglobin to DBSF between 1:2.5 to 1:4.0 for a period of time from 3 to 16 hours at ambient temperature (15-25° C.), preferably at a pH of around 8-9, such that the resultant cross-linked hemoglobin is tetrameric hemoglobin having a molecular weight of 60-70 kDa, demonstrating that polymeric hemoglobin is not present. The yield of the DBSF reaction is high, >99% and the dimer concentration in the final product is low. Optionally, the present process does not require sulfhydryl treatment reagents such as iodoacetamide to react with the hemoglobin before cross-linking as used in various prior art processes.

At this point phosphate buffered saline (PBS), a physiological buffer, is exchanged for the cross-linking solution and any residual chemicals are removed by tangential flow filtration.

Following the process of cross-linking of the hemoglobin by DBSF under a deoxygenated condition, the present invention provides a heat processing step for the cross-linked tetrameric hemoglobin solution in a deoxygenated environment. Prior to heat treatment, N-acetyl cysteine is optionally added to prevent formation of met-hemoglobin (inactive hemoglobin). After the heat processing step, the solution is cooled and N-acetyl cysteine is immediately added to maintain a low level of met-hemoglobin. If N-acetyl cysteine is added before and after heat treatment, the amount added before heat treatment is approximately 0.2%, while the amount added after heat treatment is approximately 0.2 to 0.4%. However, if N-acetyl cysteine is added only after heat treatment, then the amount added is 0.4%.

In some embodiments, the cross-linked tetrameric hemoglobin solution is heated in a deoxygenated environment (less than 0.1 ppm dissolved oxygen level) under a range of temperatures from 50° C. to 95° C. for durations from 0.5 minutes to 10 hours. In some embodiments, the cross-linked tetrameric hemoglobin solution is heated under a range of temperatures from 70° C. to 95° C. and for durations from 30 seconds to 3 hours. In some preferred embodiments, the cross-linked tetrameric hemoglobin solution is heated under 80° C. for 30 minutes. And yet in other preferred embodiments, the linked hemoglobin solution is heated to 90° C. for 30 seconds to 3 minutes, then rapidly cooled down to approximately 25° C. in approximately 15 to 30 seconds, and the N-acetyl cysteine is added as set forth above. A very low amount of met-hemoglobin results, for example, less than 3%. Without the use of N-acetyl cysteine, the amount of met-hemoglobin formed is approximately 16%, an unacceptably high percentage for pharmaceutical applications.

High performance liquid chromatography (HPLC), electrospray ionization mass spectrometry (ESI-MS), circular dichroism (CD) spectroscopy and Hemox Analyzer for p50 measurement are used thereafter to analyze and characterize the heat stable cross-linked tetrameric hemoglobin. For a bovine blood source originated hemoglobin, FIG. 4 shows that the dimeric form of hemoglobin is undetectable in a HPLC system (detection limit: 2.6 µg/ml or 0.043%) for hemoglobin which has undergone a heat treatment at 90° C. for 45 seconds to 2 minutes or 80° C. for 30 minutes. The cross-linked nonpolymeric tetrameric hemoglobin is found as heat stable at 80 or 90° C. for a period of time. The heat process (High Temperature Short Time, HTST) step is a powerful step to denature the natural unreacted tetrameric form and dimeric form of hemoglobin.

To analyze the outcome of this HTST step, a HPLC analytical method is used to detect the amount of dimer after this heat process step. The mobile phase for HPLC analysis contains magnesium chloride (0.75M) which can separate dimer (non-stabilized tetramer) and heat stable cross-linked tetrameric hemoglobin. For promoting hemoglobin dissociation into dimers, magnesium chloride is approximately 30 times more effective than sodium chloride at the same ionic strength. The heat processing step also acts as a denaturation step to dramatically remove those unwanted protein impurities in the cross-linked tetrameric hemoglobin (undetectable in immunoglobin-G; undetectable in albumin; 99.99% decrease in carbonic anhydrase). Enzyme-linked immunosorbent assay (ELISA) is performed to detect the protein impurities in the sample. Thus the purified, heat stable cross-linked tetrameric hemoglobin solution has an undetectable level of dimer (below detection limit: 0.043%), and immunoglobin-G, and a very low amount of albumin (0.02 µg/ml) and carbonic anhydrase (0.014 µg/ml). Table 2 shows the experimental results regarding the protein impurities and dimer removal by the HTST heat processing step. This HTST heat step enables the selective separation of heat stable cross-linked tetramer from unstable tetramer and dimer.

TABLE 2

| Sample condition | Protein impurities (By ELISA) | | | By HPLC | | p50 at 37° C. (mmHg) |
|---|---|---|---|---|---|---|
| | Immunoglobin-G (µg/ml) | Albumin (µg/ml) | Carbonic anhydrase (µg/ml) | Tetramer (%) | Dimer (%) | |
| No heat treatment | 0.36 | 0.57 | 355.41 | 90.1 | 5.4 | 38 |
| 80° C. for 10 min | Not detectable | 0.33 | 0.032 | 92.7 | 3.4 | No data |
| 80° C. for 15 min | Not detectable | 0.14 | 0.022 | 93.3 | 2.9 | No data |

TABLE 2-continued

| | Protein impurities (By ELISA) | | | By HPLC | | p50 at |
| | | | Carbonic | | | |
| Sample condition | Immunoglobin-G (μg/ml) | Albumin (μg/ml) | anhydrase (μg/ml) | Tetramer (%) | Dimer (%) | 37° C. (mmHg) |
| --- | --- | --- | --- | --- | --- | --- |
| 80° C. for 30 min | Not detectable | 0.03 | 0.014 | 96.6 | Not detectable | 32 |
| No heat treatment | 0.29 | 0.52 | 261.80 | 91.8 | 5.3 | 38 |
| 90° C. for 1.0 min | Not detectable | 0.21 | >0.063 | 93.4 | 2.0 | 29 |
| 90° C. for 1.5 min | Not detectable | 0.04 | 0.022 | 94.9 | 0.6 | 31 |
| 90° C. for 2.0 min | Not detectable | 0.02 | 0.016 | 96.1 | Not detectable | 31 |

Following the heat processing step for the cross-linked hemoglobin under a deoxygenated condition, the heat stable cross-linked tetrameric hemoglobin is ready for pharmaceutical formulation and packaging. The present invention describes an air-tight packaging step of the heat stable cross-linked tetrameric hemoglobin solution in a deoxygenated environment. Heat stable cross-linked tetrameric hemoglobin in the present invention is stable under deoxygenated condition for more than two years.

In this invention, the oxygen carrier-containing pharmaceutical composition is primarily intended for intravenous injection application. Traditionally, prior products use conventional PVC blood bag or Stericon blood bag which has high oxygen permeability which will eventually shorten the life span of the product since it turns into inactive met-hemoglobin rapidly (within a few days) under oxygenated conditions.

The packaging used in the present invention results in the heat stable cross-linked tetrameric hemoglobin being stable for more than two years. A multi-layer package of EVA/EVOH material is used to minimize the gas permeability and to avoid the formation of inactive met-hemoglobin. A 100 ml infusion bag designed for use with the purified and heat stable cross-linked tetrameric hemoglobin of the present invention is made from a five layers EVA/EVOH laminated material with a thickness of 0.4 mm that has an oxygen permeability of 0.006-0.132 $cm^3$ per 100 square inches per 24 hours per atmosphere at room temperature. This material is a Class VI plastic (as defined in USP<88>), which meets the in-vivo Biological Reactivity Tests and the Physico-Chemical Test and is suitable for fabricating an infusion bag for intravenous injection purpose. This primary bag is particularly useful to protect the heat stable cross-linked tetrameric hemoglobin solution from long term oxygen exposure that cause its instability and eventually affects its therapeutic properties.

For secondary protection of blood products, it has been known to use aluminum overwrap to protect against potential air leakage and to maintain the product in a deoxygenated state. However, there is a potential of pin holes in the aluminum overwrap that compromises its air tightness and make the product unstable. Therefore the present invention uses as secondary packaging an aluminum overwrap pouch which prevents oxygenation and also prevents light exposure. The composition of the overwrap pouch includes 0.012 mm of polyethylene terephthalate (PET), 0.007 mm of aluminum (Al), 0.015 mm of nylon (NY) and 0.1 mm of polyethylene (PE). The overwrap film has a thickness of 0.14 mm and an oxygen transmission rate of 0.006 $cm^3$ per 100 square inches per 24 hours per atmosphere at room temperature. This secondary packaging lengthens the stability time for the hemoglobin, extending the product shelf-life.

Figure 5:
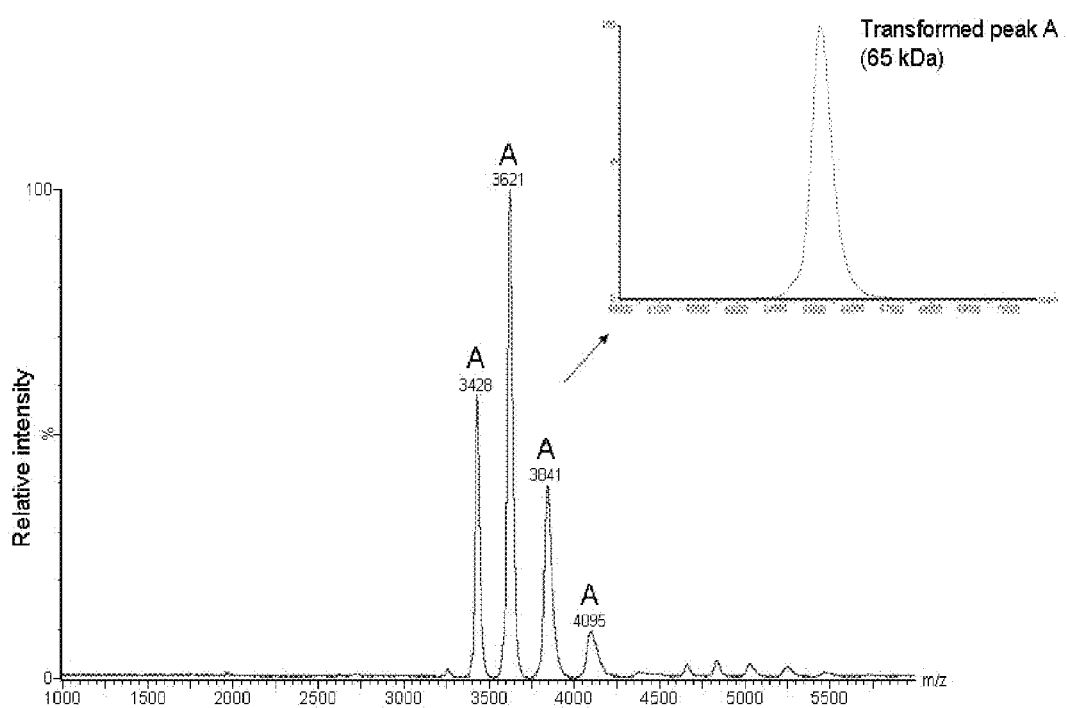
FIG. 5 depicts electrospray ionization mass spectrometry (ESI-MS) analysis for the heat stable cross-linked tetrameric hemoglobin.
Figure 6:
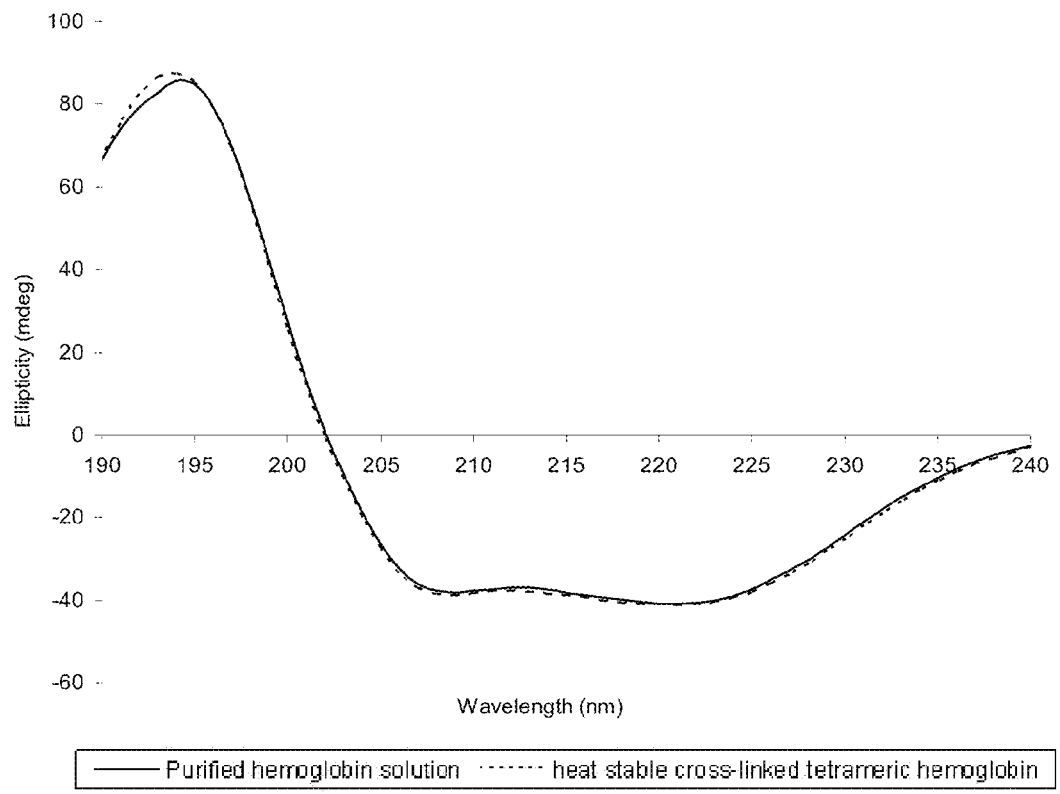
FIG. 6 shows a circular dichroism spectroscopy analysis for (a) purified hemoglobin solution and (b) heat stable cross-linked tetrameric hemoglobin.

The hemoglobin of the present invention is analyzed by various techniques, including ESI-MS. ESI-MS enables the analysis of very large molecules. It is an ionization technique that analyzes the high molecular weight compound by ionizing the protein, and then separating the ionized protein based on mass/charge ratio. Therefore, the molecular weight and the protein interactions can be determined accurately. In FIG. 5, ESI-MS analysis result indicates that the size of heat stable cross-linked tetrameric hemoglobin is 65 kDa (nonpolymeric hemoglobin tetramers). The far UV CD spectra from 190 to 240 nm reveal the secondary structures of globin portion of the hemoglobin. In FIG. 6, the consistency of the spectra of purified hemoglobin solution and heat stable cross-linked tetrameric hemoglobin reveals that the hemoglobin chains are properly folded even after the heat treatment at 90° C. The CD result shows that heat stable cross-linked tetrameric hemoglobin has around 42% of alpha-helix, 38% of beta-sheet, 2.5% of beta-turn and 16% of random coil. It further confirms that the cross-linked tetrameric hemoglobin is heat stable.

The process in this invention is applicable to large scale industrial production of the heat stable cross-linked tetrameric hemoglobin. In addition, the heat stable cross-linked tetrameric hemoglobin in combination with a pharmaceutical carrier (e.g. water, physiological buffer, in capsule form) is suitable for mammalian use.

The present invention further discloses the uses of the oxygen carrier-containing pharmaceutical composition in improving tissue oxygenation, in cancer treatment, in the treatment of oxygen-deprivation disorders such as hemorrhagic shock, and in heart preservation under a low oxygen content environment (e.g. heart transplant). The dosage is selected to have a concentration range of approximately 0.2-1.2 g/kg with an infusion rate of less than 10 ml/hour/kg body weight.

For uses in cancer treatment, the oxygen carrier-containing pharmaceutical composition of the present invention serves as a tissue oxygenation agent to improve the oxygenation in tumor tissues, thereby enhancing chemosensitivity and radiation sensitivity.

In addition, the ability of the heat stable cross-linked tetrameric hemoglobin to improve oxygenation in normal tissues (FIG. 7) and in extremely hypoxic tumors (FIG. 8), human head and neck squamous cell carcinoma (HNSCC) (using FaDu cell line) is demonstrated in this invention. The representative oxygen profile of a human FaDu xenograft is showed in FIG. 8. For oxygenation in normal tissue, oxygen partial pressure ($pO_2$) in skeletal muscle is directly monitored by a fibreoptic oxygen sensor (Oxford Optronix Limited)

coupled with a micro-positioning system (DTI Limited). After intravenous injection of 0.2 g/kg of the heat stable cross-linked tetrameric hemoglobin, the median $pO_2$ value rises from baseline to about two-fold of relative mean oxygen partial pressure within 15 minutes and extends to at least 6 hours. Further, the oxygen level on average still maintains a level of 18% to 25% above the baseline value 24 to 48 hours post infusion. No commercial products or existing technologies show as high an efficacy when compared to the oxygen carrier-containing pharmaceutical composition prepared in this invention.

Figure 8:
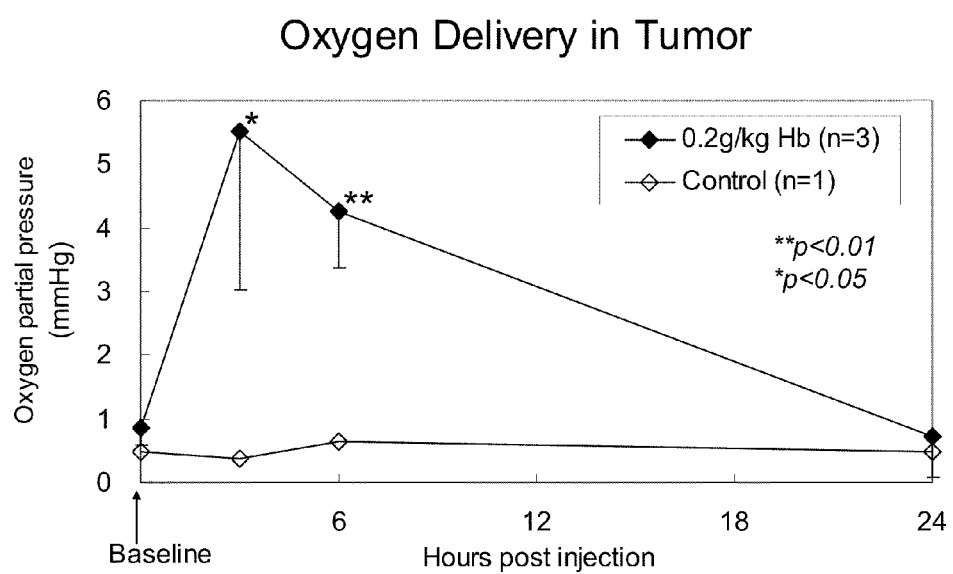
FIG. 8 shows an improvement of oxygenation in hypoxic tumor tissue. Injection of 0.2 g/kg heat stable cross-linked tetrameric hemoglobin solution results in a significant increase in oxygen delivery to the head and neck squamous cell carcinoma (HNSCC) xenograft.

For tumor tissue oxygenation, a representative oxygen profile of a human head and neck squamous cell carcinoma (HNSCC) xenograft (FaDu) is shown in FIG. 8. After intravenous injection of 0.2 g/kg of the heat stable cross-linked tetrameric hemoglobin, a significant increase in the mean $pO_2$ of more than 6.5-fold and 5-fold is observed at 3 and 6 hours, respectively (FIG. 8).

For applications in cancer treatment, the oxygen carrier-containing pharmaceutical composition of the present invention serves as a tissue oxygenation agent to improve the oxygenation in tumor tissues, thereby enhancing chemo- and radiation sensitivity. In conjunction with X-ray irradiation and the heat stable cross-linked tetrameric hemoglobin, tumor growth is delayed. In FIG. 9A, the representative curves show significant tumor shrinkage in rodent models of nasopharyngeal carcinoma. Nude mice bearing CNE2 xenografts are treated with X-ray alone (2 Gy) or in combination with the heat stable cross-linked tetrameric hemoglobin (2 Gy+Hb). 1.2 g/kg of the heat stable cross-linked tetrameric hemoglobin is injected intravenously into the mouse approximately 3 to 6 hours before X-ray irradiation and results in a partial shrinkage of nasopharyngeal carcinoma xenograft.

In one embodiment, significant liver tumor shrinkage is observed after injecting the composition, in conjunction with a chemotherapeutic agent. In FIG. 9B, the representative chart shows significant tumor shrinkage in a rat orthotopic liver cancer model. Buffalo rats bearing a liver tumor orthograft (CRL1601 cell line) are treated with 3 mg/kg cisplatin alone, or in combination with 0.4 g/kg of the heat stable cross-linked tetrameric hemoglobin (Cisplatin+Hb). Administration of the heat stable cross-linked tetrameric hemoglobin before cisplatin injection results in a partial shrinkage of the liver tumor.

For the use in the treatment of oxygen-deprivation disorders and for heart preservation, the oxygen carrier-containing pharmaceutical composition of the present invention serves as a blood substitute providing oxygen to a target organ.

Figure 10:
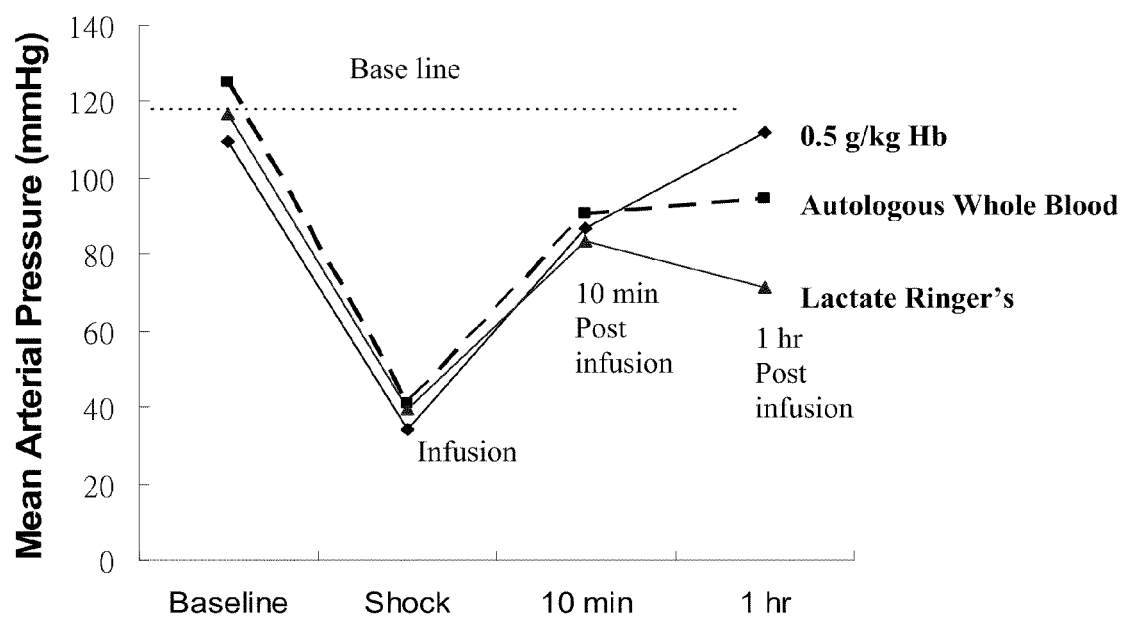
FIG. 10 demonstrates the mean arterial pressure changes in a rat model of severe hemorrhagic shock after the treatment with the heat stable cross-linked tetrameric hemoglobin.

The mean arterial pressure changes in a rat model of severe hemorrhagic shock after treatment with 0.5 g/kg of the heat stable cross-linked tetrameric hemoglobin are shown in FIG. 10. In a rat model of severe hemorrhagic shock, the mean arterial pressure is returned back to a safe and stable level and maintained at or about the baseline after treatment with the heat stable cross-linked tetrameric hemoglobin. Following treatment with the heat stable cross-linked tetrameric hemoglobin, the time required for the mean arterial pressure to return to normal is even shorter than administrating autologous rat's blood which serves as a positive control. The results indicate that a vasoconstriction event does not occur after the transfusion of the heat stable cross-linked tetrameric hemoglobin.

EXAMPLES

The following examples are provided by way of describing specific embodiments of this invention without intending to limit the scope of this invention in any way.

Example 1

Process Overview

A schematic flow diagram of the process of the present invention is illustrated in FIG. 2. Bovine whole blood is collected into an enclosed sterile container/bag containing 3.8% (w/v) tri-sodium citrate solution as anti-coagulant. Blood is then immediately mixed well with tri-sodium citrate solution to inhibit blood clotting. Red blood cells (RBC) are isolated and collected from plasma and other smaller blood cells by an apheresis mechanism. A "cell washer" is used for this procedure with gamma sterilized disposable centrifuge bowl. RBC are washed with an equal volume of 0.9% (w/v sodium chloride) saline.

Washed RBC are lysed to release hemoglobin content by manipulating hypotonic shock to the RBC cell membrane. A specialized instant cytolysis apparatus for RBC lysis device depicted in FIG. 3 is used for this purpose. Following RBC lysis, hemoglobin molecules are isolated from other proteins by tangential-flow ultrafiltration using a 100 kDa membrane. Hemoglobin in the filtrate is collected for flowthrough column chromatography and further concentrated to 12-14 g/dL by a 30 kDa membrane. Column chromatography is carried out to remove the protein impurities.

The concentrated hemoglobin solution is first reacted with DBSF to form heat stable cross-linked tetrameric hemoglobin molecules under a deoxygenated condition. A heat treatment step is then performed under deoxygenated conditions at 90° C. for 30 seconds to three minutes before final formulation and packaging.

Example 2

Time & Controlled Hypotonic lysis and filtration

Bovine whole blood is freshly collected and transported under a cool condition (2 to 10° C.). The red blood cells are separated from the plasma via a cell washer and subsequently with a 0.65 µm filtration. After washing the red blood cells (RBC) filtrate with 0.9% saline, the filtrate is disrupted by hypotonic lysis. The hypotonic lysis is performed by using the instant cytolysis apparatus depicted in FIG. 3. The instant cytolysis apparatus includes a static mixer to assist in cell lysis. A RBC suspension with controlled hemoglobin concentration (12-14 g/dL) is mixed with 4 volumes of purified water to generate a hypotonic shock to RBC cell membranes. The period of hypotonic shock is controlled to avoid unwanted lysis of white blood cells and platelets. The hypotonic solution passes through the static mixer portion of the instant cytolysis apparatus for 2 to 30 seconds or otherwise a time sufficient to lyse the red blood cells and preferably, 30 seconds. The shock is terminated after 30 seconds by mixing the lysate with 1/10 volume of hypertonic buffer as it exits the static mixer. The hypertonic solution used is 0.1M phosphate buffer, 7.4% NaCl, pH 7.4. The instant cytolysis apparatus of FIG. 3 can process at 50 to 1000 liters of lysate per hour and, preferably at least 300 liters per hour in a continuous manner.

Following the RBC lysis, the lysate of red blood cells is filtered by a 0.22 µm filter to obtain a hemoglobin solution. Nucleic acids from white blood cells and phospholipids impurities are not detected in the hemoglobin solution by polymerase chain reaction (detection limit=64 pg) and HPLC (detection limit=1 µg/ml) method respectively. A first 100 kDa ultrafiltration is performed to remove impurities having a higher molecular weight than hemoglobin. A flowthrough column chromatography is followed to further purify the hemoglobin solution. A second 30 kDa ultrafiltration is then performed to remove impurities having a lower molecular weight than hemoglobin and for concentration.

Example 3

Viral Clearance Study on Stroma-Free Hemoglobin Solution

In order to demonstrate the safety of the product from this invention, the virus removal abilities of (1) 0.65 µm diafiltration step and (2) 100 kDa ultrafiltration step are demonstrated by virus validation study. This is done by the deliberate spiking of a down-scaled version of these two processes with different model viruses (encephalomyocarditis virus, pseudorabies virus, bovine viral diarrhea virus and bovine parvovirus). In this study, four types of viruses (see Table 3) are used. These viruses vary in their biophysical and structural features and they display a variation in resistance to physical and chemical agents or treatments.

The validation scheme is briefly shown in the following Table 4.

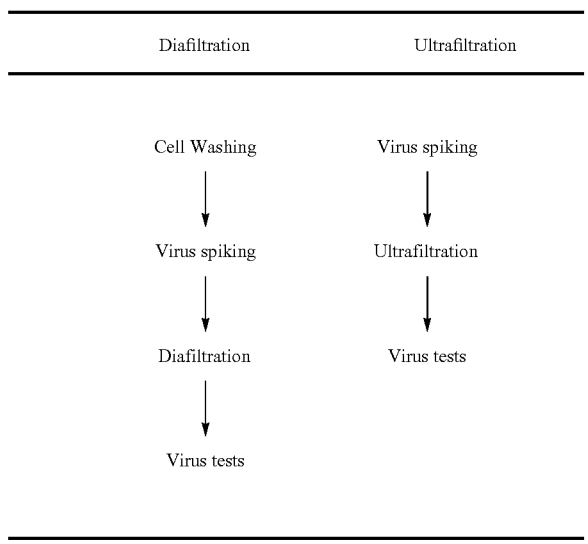

TABLE 4

TABLE 3

| Target Virus | Model Virus | Taxonomy | Genome | Structure | Size [nm] | Stability* |
|---|---|---|---|---|---|---|
| Hepatitis C virus (HCV) | Bovine viral diarrhea virus (BVDV) | Flaviviridae | ssRNA | enveloped | 40-60 | low |
| — | Encephalomyocarditis virus (EMCV) | Picornavirus | ssRNA | non-enveloped | 25-30 | medium |
| Parvovirus B19 | Bovine parvovirus (BPV) | Parvoviridae | ssDNA | non-enveloped | 18-26 | very high |
| Hepatitis B virus (HBV) | Pseudorabies virus (PRV) | Herpesviridae | dsDNA | enveloped | 120-200 | Low to medium |

The summary of the log reduction results of the 4 viruses in (1) 0.65 µm diafiltration and (2) 100 kDa ultrafiltration is shown in the following Table 5. All four viruses, BVDV, BPV, EMCV and PRV, are effectively removed by 0.65 µm diafiltration and 100 kDa ultrafiltration.

| Viruses | BVDV | | BPV | | EMCV | | PRV | |
|---|---|---|---|---|---|---|---|---|
| Run | 1 | 2 | 1 | 2 | 1 | 2 | 1 | 2 |
| 0.65 µm Diafiltration | 2.69 | 3.20 | 3.73 | 3.53 | 3.25 | ≧3.90 | 2.67 | 2.63 |
| 100 kDa Ultrafiltration | ≧4.68 | ≧4.38 | 5.87 | 5.92 | 3.60 | 3.43 | ≧6.05 | 3.27 |
| Cumulative maximum | ≧7.88 | | 9.65 | | ≧7.50 | | ≧8.72 | |
| Cumulative minimum | ≧7.07 | | 9.40 | | 6.68 | | 5.90 | |

Annotation:

≧no residual infectivity determined

Example 4

Flowthrough Column Chromatography

Figure 11:
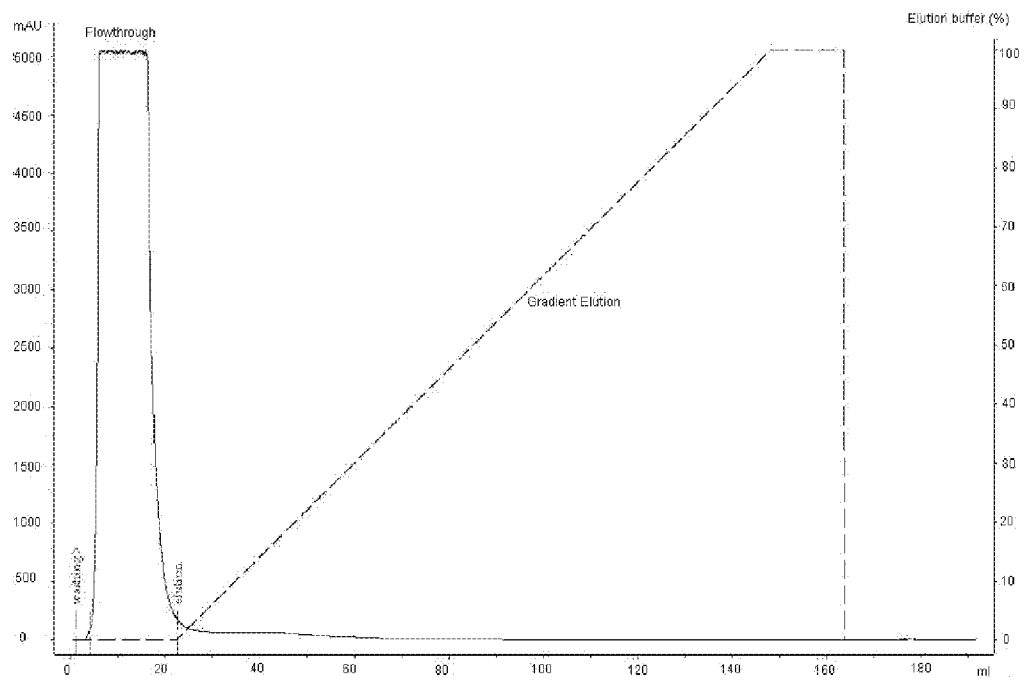
FIG. 11 is an elution profile for flowthrough column chromatography; the hemoglobin solution is in the flowthrough fraction.

A CM column (commercially available from GE healthcare) is used to further remove any protein impurities. The starting buffer is 20 mM sodium acetate (pH 8.0), and the elution buffer is 20 mM sodium acetate, 2M NaCl (pH 8.0). After the equilibration of the CM column with starting buffer, the protein sample is loaded into the column. The unbound protein impurities are washed with at least 5 column volume of starting buffer. The elution is performed using 25% elution buffer (0-0.5M NaCl) in 8 column volume. The elution profile is shown in FIG. 11; the hemoglobin solution is in the flowthrough fraction. The purity of the flowthrough fraction is analyzed by ELISA. The results are indicated in the following Table 6.

TABLE 6

|  | Protein impurities | | |
| --- | --- | --- | --- |
|  | Immunoglobin-G | Carbonic anhydrase | Albumin |
| Before CM column | 1320 ng/ml | 860.3 µg/ml | 435.2 ng/ml |
| Flowthrough (containing hemoglobin) | 44.3 ng/ml | 81.2 µg/ml | 20.4 ng/ml |

Figure 12:
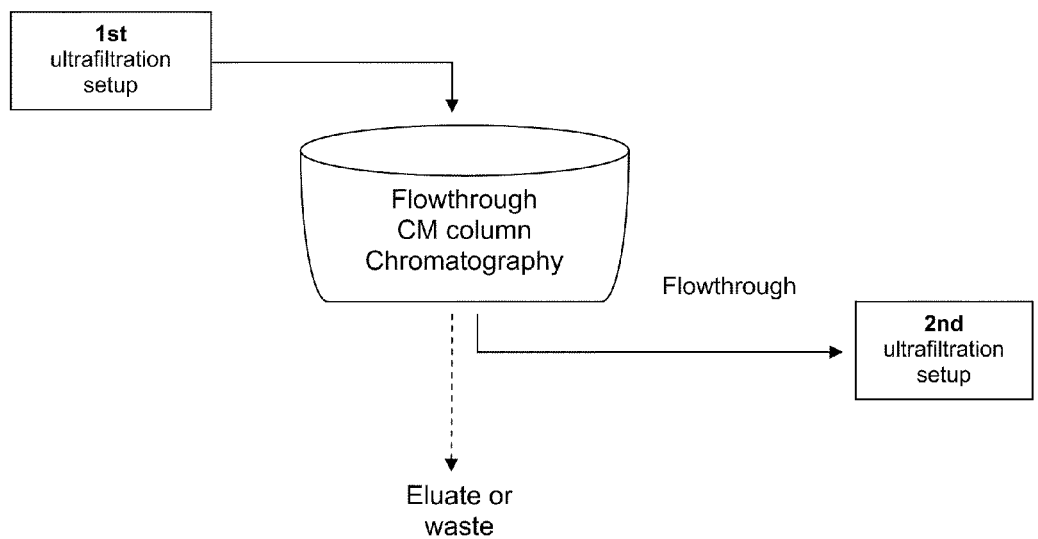
FIG. 12 schematically depicts a flowthrough CM column chromatography system with ultrafiltration for an industrial scale operation.

As the hemoglobin solution is in the flowthrough from the CM column chromatography at pH 8 (not in the eluate), it is a good approach for continuous industrial scale operation. The first ultrafiltration set-up is connected directly to the flowthrough CM column chromatography system, and the flowthrough tubing can be connected to the second ultrafiltration set-up for industrial scale operation. The schematic industrial process configuration is shown in FIG. 12.

Example 5

Preparation of Heat Stable Cross-Linked Tetrameric Hemoglobin (5a) Cross-Linking Reaction with DBSF The cross-linking reaction is carried out in a deoxygenated condition. DBSF is added to the hemoglobin solution to form cross-linked tetrameric hemoglobin without formation of polymeric hemoglobin. DBSF stabilization procedure stabilizes the tetrameric form of hemoglobin (65 kDa) and prevents dissociation into dimers (32 kDa) which are excreted through the kidneys. In this embodiment, a molar ratio of hemoglobin to DBSF of 1:2.5 is used and the pH is 8.6. This process is carried out for a period of 3-16 hours at ambient temperature (15-25° C.) in an inert atmosphere of nitrogen to prevent oxidation of the hemoglobin to form ferric met-hemoglobin which is physiologically inactive (dissolved oxygen level maintained at less than 0.1 ppm). The completeness of DBSF reaction is monitored by measuring the residual DBSF using HPLC. The yield of the DBSF reaction is high, >99%.

(5b) HTST Heat Process Step

Figure 13:
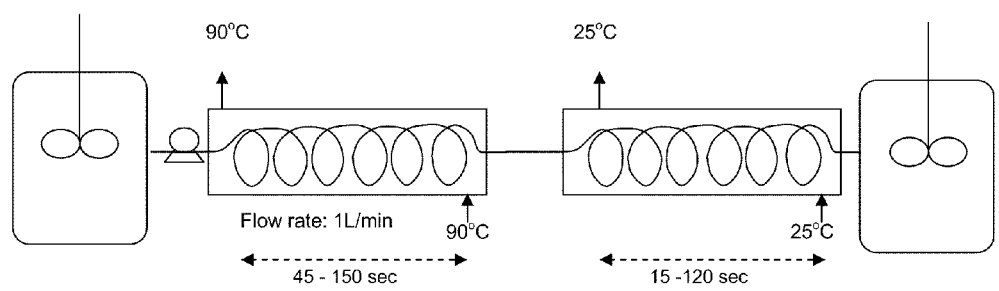
FIG. 13 is a schematic depiction of an apparatus used for HTST heat treatment processing step.
Figure 14:
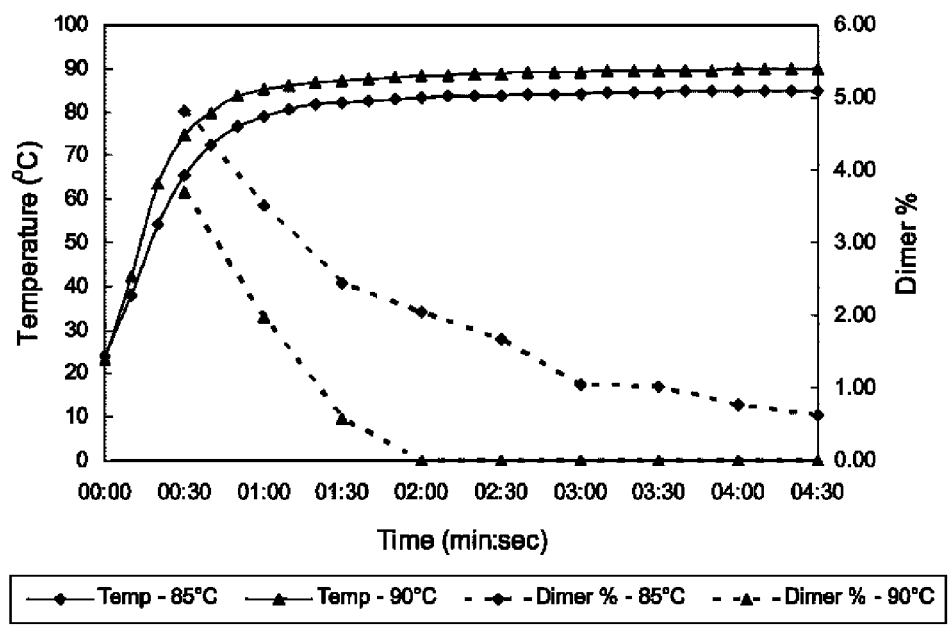
FIG. 14 demonstrates the temperature profile in the HTST processing apparatus and the time taken to remove unstabilized tetramer (dimer) in the system at 85° C. and 90° C. of the present invention.

A High Temperature Short Time (HTST) processing apparatus is shown in FIG. 13. A heating process using the HTST processing apparatus is performed on the cross-linked tetrameric hemoglobin. In this example, the condition for heat treatment is 90° C. for 30 seconds to 3 minutes, and preferably 45 to 60 seconds although other conditions can be selected as discussed above and the apparatus modified accordingly. A solution containing cross-linked hemoglobin optionally with 0.2% of N-acetyl cysteine added thereto is pumped into a HTST processing apparatus (first section of the HTST heat exchanger is pre-heated and maintained at 90° C.) at a flow rate of 1.0 liter per minute, the residence time of the first section of the apparatus is between 45 to 60 seconds, then the solution is passed through at the same flow rate into another section of the heat exchanger that is maintained at 25° C. The time required for cooling is between 15 to 30 seconds. After cooling down to 25° C., N-acetyl cysteine is immediately added at a concentration of 0.2% to 0.4%, preferably at 0.4%. This chemical addition after the HTST heating process is very important to maintain met-hemoglobin (inactive hemoglobin) at a low level. The set-up of the processing apparatus is easily controlled for industrial operation. A temperature profile with dimer content is shown in FIG. 14. If the hemoglobin is not cross-linked, it is not heat stable and forms a precipitate after the heat step. The precipitate is then removed by a centrifugation or a filtration apparatus to form a clear solution thereafter.

Figure 15:
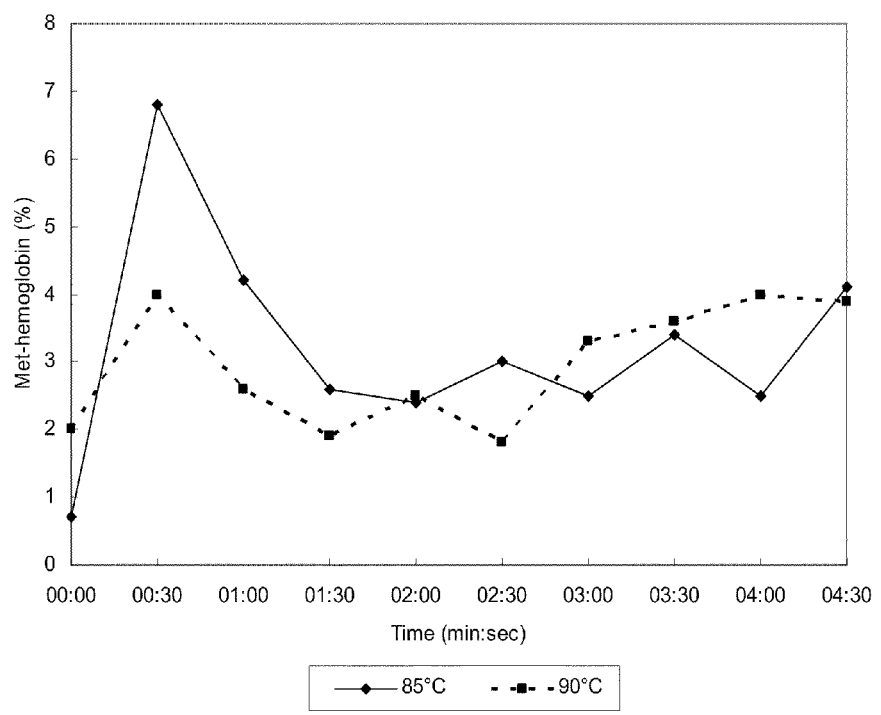
FIG. 15 demonstrates the rate of met-hemoglobin formation in the system at 85° C. and 90° C. in the HTST processing apparatus of FIG. 13.

During the HTST heating process at 90° C., met-hemoglobin (inactive hemoglobin) is increased (shown in FIG. 15). After immediate addition of N-acetyl cysteine, a low level of met-hemoglobin, approximately less than 3%, can be maintained.

The following Table 7 shows that protein impurities such as immunoglobin-G, albumin, carbonic anhydrase and undesirable non-stabilized tetramer or dimers are removed after the heat treatment step. The amount of immunoglobin-G, albumin and carbonic anhydrase are measured using an ELISA method, while the amount of dimer is determined by an HPLC method. The purity of heat stable cross-linked tetrameric hemoglobin is extremely high after the HTST heating processing step, in the range of 98.0 to 99.9%. The p50 value, oxygen partial pressure (at which the hemoglobin solution is half (50%) saturated) measured by a Hemox Analyzer, is maintained at around 30 to 40 mmHg throughout the HTST heating processing step and therefore, the heat treated cross-linked tetrameric hemoglobin is stable at 90° C.

TABLE 7

| | Protein impurities (by ELISA) | | | By HPLC | | p50 at |
| --- | --- | --- | --- | --- | --- | --- |
| Sample condition | Immunoglobin-G (µg/ml) | Albumin (µg/ml) | Carbonic anhydrase (µg/ml) | Tetramer (%) | Dimer (%) | 37° C. (mm Hg) |
| No heat treatment | 0.29 | 0.52 | 261.80 | 91.8 | 5.3 | 38 |
| 90° C. for 2 min | Not detectable | 0.02 | 0.016 | 96.1 | Not detectable | 31 |
| Removal (%) | 100.0 | 96.15 | 99.99 | — | 100.0 | — |

Example 6

Packaging

Figure 16:
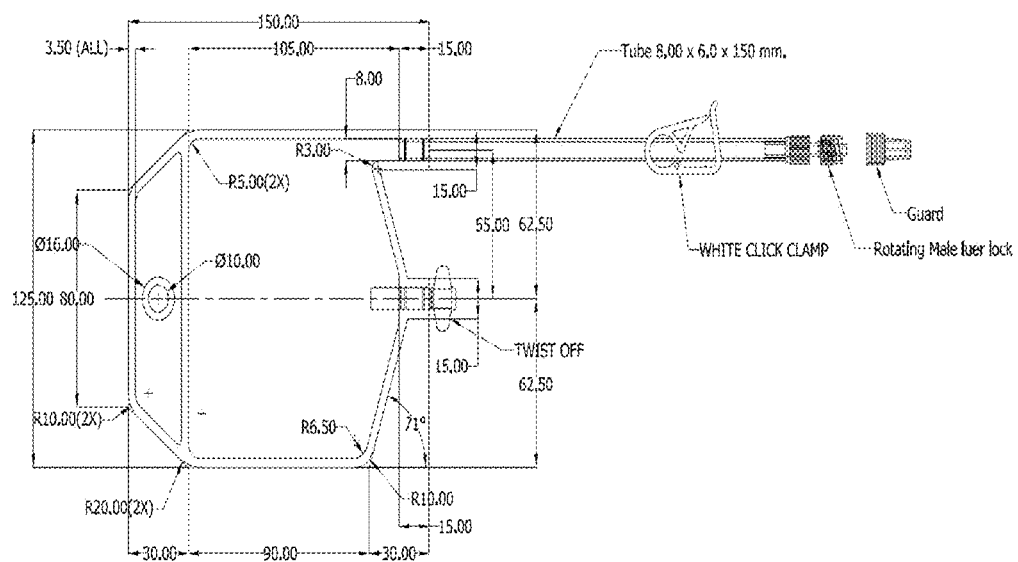
FIG. 16 is a schematic depiction of an infusion bag for the heat stable cross-linked tetrameric hemoglobin of the present invention.

Because the product of the present invention is stable under deoxygenated conditions, the packaging for the product is important to minimize gas permeability. For intravenous application, a custom designed, 100 ml infusion bag is made from a five-layer EVA/EVOH laminated material with a thickness of 0.4 mm that has an oxygen permeability of 0.006 to 0.132 cm$^3$ per 100 square inches per 24 hours per atmosphere at room temperature. This specific material is a Class VI plastic (as defined in USP<88>), which meets the in-vivo biological reactivity tests and the physico-chemical test and are suitable for fabricating containers for intravenous injection purpose (note that other forms of packaging can be made from this material as well depending upon the desired application). A secondary packaging aluminum overwrap pouch is also applied to the primary packaging infusion bag that provides an additional barrier, minimizing light exposure and oxygen diffusion. The layers of the pouch comprise: 0.012 mm of Polyethylene terephthalate (PET), 0.007 mm of Aluminum (Al), 0.015 mm of Nylon (NY) and 0.1 mm of Polyethylene (PE). The overwrap film has a thickness of 0.14 mm and oxygen transmission rate of 0.006 cm$^3$ per 100 square inches per 24 hours per atmosphere at room temperature. A schematic depiction of the infusion bag is depicted in FIG. 16. The overall oxygen permeability for each infusion bag according to the present invention is 0.0025 cm$^3$ per 24 hours per atmosphere at room temperature.

Example 7

Improvement of Oxygenation (7a) Improvement of Oxygenation in Normal Tissue Some studies for the normal tissue oxygenation by heat stable cross-linked tetrameric hemoglobin are carried out (shown in FIG. 7). A comparative pharmacokinetic and pharmacodynamic study is conducted in buffalo rats. Male inbred buffalo rats are individually administered with 0.2 g/kg heat stable cross-linked tetrameric hemoglobin solution or ringer's acetate buffer (control group), through intravenous injection into the rats. The concentration-time profile of plasma hemoglobin is determined by Hemocue™ photometer at 1, 6, 24, 48 hours and compared with the baseline reading. The methods are based on photometric measurement of hemoglobin where the concentration of hemoglobin is directly read out as g/dL. Oxygen partial pressure (pO$_2$) is directly measured by the Oxylab™ tissue oxygenation and temperature monitor (Oxford Optronix Limited) in hind leg muscle of buffalo rats. Rats are anesthetized by intra-peritoneal injection of 30-50 mg/kg pentobarbitone solution followed by insertion of oxygen sensor into the muscle. All pO$_2$ readings are recorded by Datatrax2 data acquisition system (World Precision Instrument) in a real-time manner. Results demonstrate that after an intravenous injection of 0.2 g/kg of the heat stable cross-linked tetrameric hemoglobin, the mean pO$_2$ value rises from baseline to about two-fold of the relative mean oxygen partial pressure within 15 minutes and extends to 6 hours. Further, the oxygen level on average is still maintained at 18% to 25% above the baseline value 24 to 48 hours post injection (FIG. 7B).

(7b) Significant Improvement of Oxygenation in Extremely Hypoxic Tumor Area

Improvement of oxygenation in an extremely hypoxic tumor area is evaluated by a human head and neck squamous cell carcinoma (HNSCC) xenograft model. A hypopharyngeal squamous cell carcinoma (FaDu cell line) is obtained from the American Type Culture Collection. Approximately 1×10$^6$ cancer cells are injected subcutaneously into four to six week-old inbred BALB/c AnN-nu (nude) mice. When the tumor xenograft reaches a diameter of 8-10 mm, oxygen partial pressure (pO$_2$) within the tumor mass is directly monitored by the Oxylab™ tissue oxygenation and temperature monitor (Oxford Optronix Limited). All pO$_2$ readings are recorded by the Datatrax2 data acquisition system (World Precision Instrument) in a real-time manner. When the pO$_2$ reading is stabilized, 0.2 g/kg heat stable cross-linked tetrameric hemoglobin solution is injected intravenously into the mice and the tissue oxygenation is measured. Results demonstrate that after intravenous injection of 0.2 g/kg of the said heat stable cross-linked tetrameric hemoglobin, a significant increase in the mean pO$_2$ of more than 6.5-fold and 5-fold is observed in 3 and 6 hours, respectively (FIG. 8).

Example 8

Cancer Treatment Studies

A Significant Tumor Shrinkage in Nasopharyngeal Carcinoma

A significant tumor shrinkage is observed after administration of heat stable cross-linked tetrameric hemoglobin solution in combination with X-ray irradiation (FIG. 9A). A human nasopharyngeal carcinoma xenograft model is employed. Approximately 1×10$^6$ cancer cells (CNE2 cell line) are injected subcutaneously into four to six week-old inbred BALB/c AnN-nu (nude) mice. When the tumor xenograft reaches a diameter of 8-10 mm, tumor-bearing mice are randomized into three groups as follows:

Group 1: Ringer's acetate buffer (Ctrl)
Group 2: Ringer's acetate buffer+X-ray irradiation (2 Gy)
Group 3: Heat stable cross-linked tetrameric hemoglobin+X-ray irradiation (2 Gy+Hb)

Nude mice bearing CNE2 xenografts are irradiated with X-irradiation alone (Group 2) or in combination with heat stable cross-linked tetrameric hemoglobin (Group 3). For X-ray irradiation (Groups 2 and 3), mice are anesthetized by an intra-peritoneal injection of 50 mg/kg pentobarbitone solution. 2 Grays of X-ray is delivered to the xenograft of tumor-bearing mice by a linear accelerator system (Varian Medical Systems). For Group 3, 1.2 g/kg heat stable cross-linked tetrameric hemoglobin is injected intravenously into the mouse before X-ray treatment. Tumor dimensions and body weights are recorded every alternate day starting with the first day of treatment. Tumor weights are calculated using the equation ½LW$^2$, where L and W represent the length and width of the tumor mass, measured by a digital caliper (Mitutoyo Co, Tokyo, Japan) at each measurement. Group 1 is the non-treatment control group. Results (shown in FIG. 9) demonstrate that significant shrinkage of the CNE2 xenograft is observed in mice treated with the heat stable cross-linked tetrameric hemoglobin solution in conjunction with X-irradiation (Group 3, FIG. 9A).

Example 9

Cancer Treatment Studies

A Significant Shrinkage in Liver Tumor

In addition, significant tumor shrinkage is observed after administration of heat stable cross-linked tetrameric hemoglobin solution in combination with cisplatin (FIG. 9B). A rat orthotopic liver cancer model is employed. Approximately $2 \times 10^6$ rat liver tumor cells labeled with luciferase gene (CRL1601-Luc) are injected into the left lobe of the liver in a buffalo rat. Tumor growth is monitored by a Xenogen in vivo imaging system. Two to three weeks after injection, the tumor tissue is harvested, dissected into small pieces and orthotopically implanted into the left liver lobe of a second group of rats. Rats bearing liver tumor are randomized into three groups as follows:

Group 1: Ringer's acetate buffer (Control)

Group 2: Ringer's acetate buffer+cisplatin (Cisplatin)

Group 3: Heat stable cross-linked tetrameric hemoglobin+ cisplatin (Cisplatin+Hb)

Rats implanted with liver tumor tissue are treated with 3 mg/kg of cisplatin alone (Group 2) or in conjunction with heat stable cross-linked tetrameric hemoglobin (Group 3). For groups 2 and 3, rats are anesthetized by an intra-peritoneal injection of 30-50 mg/kg pentobarbitone solution and cisplatin are administered via the left portal vein. For Group 3, 0.4 g/kg heat stable cross-linked tetrameric hemoglobin is injected intravenously into the rat before cisplatin treatment. Group 1 is the non-treatment control group. Importantly, a significant shrinkage of liver tumor is observed 3 weeks after treatment (FIG. 9B).

Example 10

Treatment of Acute Severe Hemorrhagic Shock in Rats

Heat stable cross-linked tetrameric hemoglobin is also used as a resuscitation agent in a model of Acute Severe Hemorrhagic Shock in rats. 50 Sprague-Dawley rats are randomly divided into 3 groups according to resuscitation agents, 16 to 18 rats in each group.

Group 1: Lactate Ringer's solution (Negative Control, 16 rats)

Group 2: Animal autologous blood (Positive Control, 16 rats)

Group 3: Heat stable cross-linked tetrameric hemoglobin treatment group (0.5 g Hb/kg of body weight, 18 rats)

Acute severe hemorrhagic shock is established by withdrawing 50% of animal whole blood, which is estimated as 7.4% of body weight. After hemorrhagic shock is established for 10 minutes, Lactate Ringer's solution, animal autologous blood, or 0.5 g Hb/kg of heat stable cross-linked tetrameric hemoglobin are infused into the animals. The infusion rate of heat stable cross-linked tetrameric hemoglobin is set at 5 ml/h, thereafter, all experimental animals are observed for 24 hours. A panel of parameters is observed and analyzed during study period including survival, hemodynamics, myocardial mechanics, cardiac output, cardiac function, blood gas, tissue oxygen delivery & consumption, tissue perfusion & oxygen tension (liver, kidney and brain), liver & renal function, hemorheology (blood viscosity), and mitochondrial respiratory control rate (liver, kidney and brain). Above all, survival is the primary end point. After 24 hours of observation, the heat stable cross-linked tetrameric hemoglobin treatment group has a much higher survival rate compared with the Lactate Ringer's solution or negative control group and the autologous blood group (shown in the following Table 8).

TABLE 8

| Groups | Survival no. after 24-hour | 24-hour survival rate (%) |
|---|---|---|
| Negative control | 3 in 16 rats | 18.8 |
| Rat's Autologous Blood | 10 in 16 rats | 62.5 |
| 0.5 g Hb/kg | 13 in 18 rats | 72.0 |

*Hb = heat stable cross-linked tetrameric hemoglobin

Example 11

Method of Preventing Post-Operative Liver Tumor Recurrence and Metastasis

Surgical resection of liver tumors is a frontline treatment of liver cancer. However, post-operative recurrence and metastasis of cancer remains a major attribute of unfavorable prognosis in these patients. For instance, previous studies reported that hepatic resection is associated with a 5-year survival rate of 50% but also a 70% recurrence rate. Follow-up studies on hepatocellular carcinoma (HCC) patients also reveal that extrahepatic metastases from primary HCC were detected in approximately 15% of HCC patients with the lungs being the most frequent site of extrahepatic metastases. It has been suggested that surgical stress, especially ischemia/reperfusion (IR) injury introduced during liver surgery is a major cause of tumor progression. Conventionally, hepatic vascular control is commonly used by surgeons to prevent massive hemorrhage during hepatectomy. For example, inflow occlusion by clamping of the portal triad (Pringle maneuver) has been used to minimize blood loss and reduce the requirement of perioperative transfusions. A recent Japanese study shows that 25% surgeons apply a Pringle maneuver on a routine basis. However, Pringle maneuver induces various degrees of ischemic injury in the remnant liver and is associated with cancer recurrence and metastasis.

Association of IR injury and tumor progression is also supported by previous animal studies. Firstly, the effect of IR injury and hepatic resection on liver cancer recurrence and metastasis was demonstrated in a recent study with an orthotopic liver cancer model. Hepatic IR injury and hepatectomy resulted in prominent recurrence and metastasis of liver tumors. Similar results were obtained in a colorectal liver metastasis mouse model where introduction of IR injury accelerates the outgrowth of colorectal liver metastasis.

Previously, several protective strategies have been studied for use to reduce IR injury during resection. For example, the application of a short period of ischemia before prolonged clamping, known as ischemic preconditioning (IP), was suggested to trigger hepatocellular defense mechanisms and has been used to reduce IR injury during liver resection. Others apply intermittent clamping (IC) procedures which allows cycles of inflow occlusion followed by reperfusion. Both methods were suggested to be effective in protecting against postoperative liver injury in non-cirrhotic patients undergoing major liver surgery. However, in a tumor setting, animal studies also show that IP failed to protect the liver against accelerated tumor growth induced by IR injury. In addition, some groups attempt to use anti-oxidants such as α-tocopherol and ascorbic acid to protect the liver from IR injury, thereby preventing liver metastasis. However, both anti-oxidants failed to restrict intrahepatic tumor growth stimulated by IR.

Mechanistically, different lines of evidence suggest hypoxia is associated with tumor recurrence and metastasis for a number of reasons: (1) studies show that hypoxic tumor is more resistant to radiation- and a chemo-therapy, tumor cells that survive the treatment are prone to recur; clinical evidence also suggests that patients with more hypoxic tumor areas have higher rates of metastases; (2) under hypoxic condition, cancer cells become more aggressive through the activation of hypoxia inducible factor-1 (HIF-1) pathway. This in turn triggers complementary responses involving pro-angiogenic factor vascular endothelial growth factor (VEGF) and receptors such as c-Met and CXCR4, which enhanced cell motility and homing to specific, distant organs; (3) recent studies also demonstrated that circulating cancer cells (CTCs) become more aggressive under hypoxic condition. Circulating tumor cells detected in the peripheral blood of cancer patients was shown to be an index of disease aggression in patients with distant metastasis, while hypoxia enabled those cells a more aggressive phenotype and diminished apoptotic potential. In particular, cancer stem cell population, which is more radio-resistant were enriched under reduced oxygen level in brain tumor.

Figure 17:
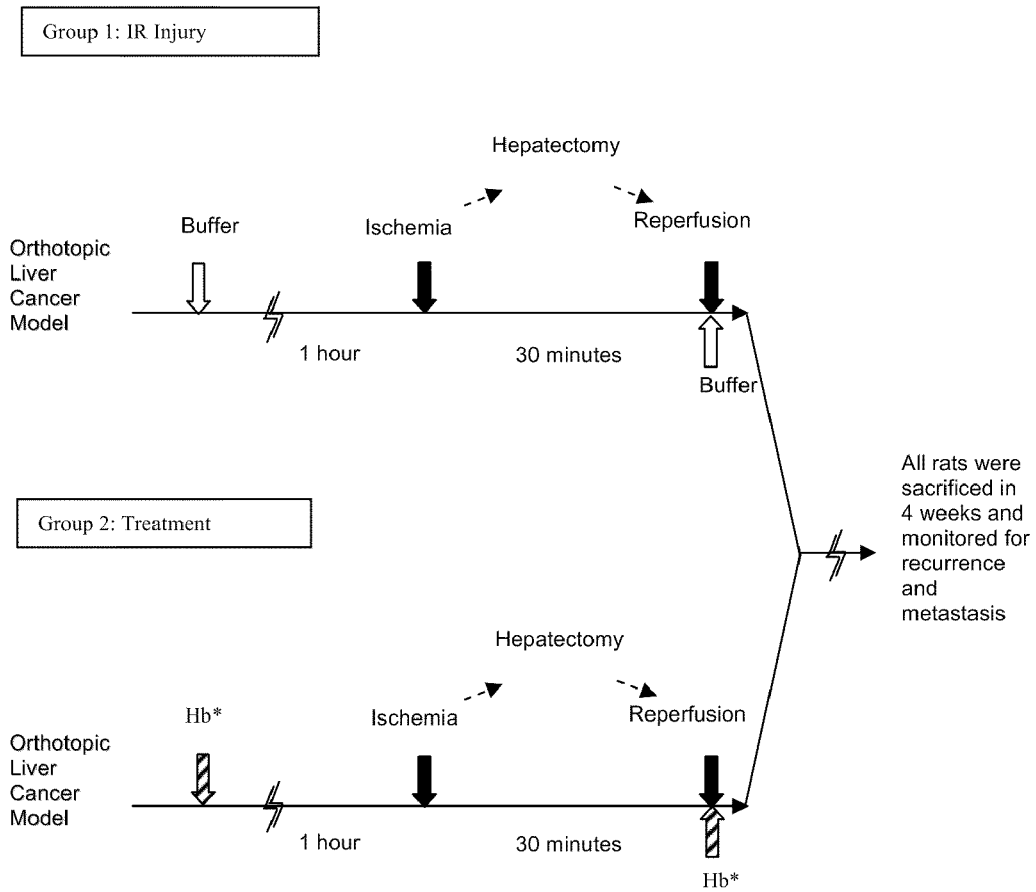
FIG. 17 shows a schematic drawing summarizing the surgical and hemoglobin product administration procedures during liver resection.

Therefore, in view of the above observations and studies, the heat stable cross-linked tetrameric hemoglobin of the present invention is used to prevent post-operative liver tumor recurrence and metastasis following hepatic resection. A rat orthotopic liver cancer model is established. Hepatocellular carcinoma cell line (McA-RH7777 cells) is used to establish the orthotopic liver cancer model in Buffalo rats (Male, 300-350 g). FIG. 17 shows a schematic drawing summarizing the surgical and hemoglobin product administration procedures. McA-RH7777 cells ($3 \times 10^5/100$ µl) are injected into the hepatic capsule of buffalo rat to induce solid tumor growth. Two weeks later (when the tumor volume reaches about $10 \times 10$ mm), tumor tissue is collected and cut into 1-2 mm$^3$ cubes and implanted into the left liver lobes of a new group of buffalo rats. Two weeks after orthotopic liver tumor implantation, the rats undergo liver resection (left lobe bearing liver tumor) and partial hepatic IR injury (30 minutes of ischemia on right lobe).

Two groups of rats with implanted tumor tissue are used for comparison of tumor recurrence and metastases. In group 1, rats are anesthetized with pentobarbital and administered intravenously with 0.2 g/kg of the nonpolymeric heat stable cross-linked tetrameric hemoglobin of the present invention 1 hour before ischemia. However, it is contemplated that ranges on the order of 0.2 g/kg-1.2 g/kg can be used in this process. Further, the time may range from a period on the order of several hours to on the order of several minutes (e.g., 30 minutes) prior to ischemia. Ischemia is introduced in the right lobe of the liver by clamping of right branches of hepatic portal vein and hepatic artery with a bulldog clamp. Subsequently, ligation is performed in the left liver lobe followed by resection of the left liver lobe bearing the liver tumor. At 30 minutes after ischemia, an additional 0.2 g/kg of the heat stable cross-linked tetrameric hemoglobin is injected through the inferior vena cava followed by reperfusion. In group 2, ringer's acetate buffer is injected as a vehicle control with the same procedure. All rats are sacrificed 4 weeks after the hepatectomy procedures.

To examine tumor growth and metastasis, the liver and lungs of Buffalo rats are sampled at 4 weeks after Ischemia/reperfusion and hepatectomy procedures for morphological examination. Tissue is harvested, parafilm-embedded and sectioned followed by Hematoxylin and Eosin (H&E) staining Local recurrence/metastasis (intrahepatic) and distant metastasis (lungs) are confirmed by histological examination. Table 9 summarizes the observations.

TABLE 9

Comparison of tumor recurrence/metastasis at four weeks after liver resection and IR injury in a rat orthotopic liver cancer model.

| | Control (n = 6) | Treatment (n = 5) |
|---|---|---|
| Intrahepatic metastasis/recurrence | 4 (66.7%) | 2 (40%) |
| Lung metastasis | 4 (66.7%) | 2 (40%) |

To examine the protective effects of nonpolymeric heat stable cross-linked tetrameric hemoglobin on liver tumor recurrence and metastasis, all rats are sacrificed 4 weeks after the hepatectomy and IR procedures. Lungs and liver tissues are harvested; hepatic tumor recurrence/metastasis and distant metastasis in the lungs are compared in both groups. Results show that the hemoglobin treatment decreases occurrence of recurrence and metastasis in both organs.

Figure 18:
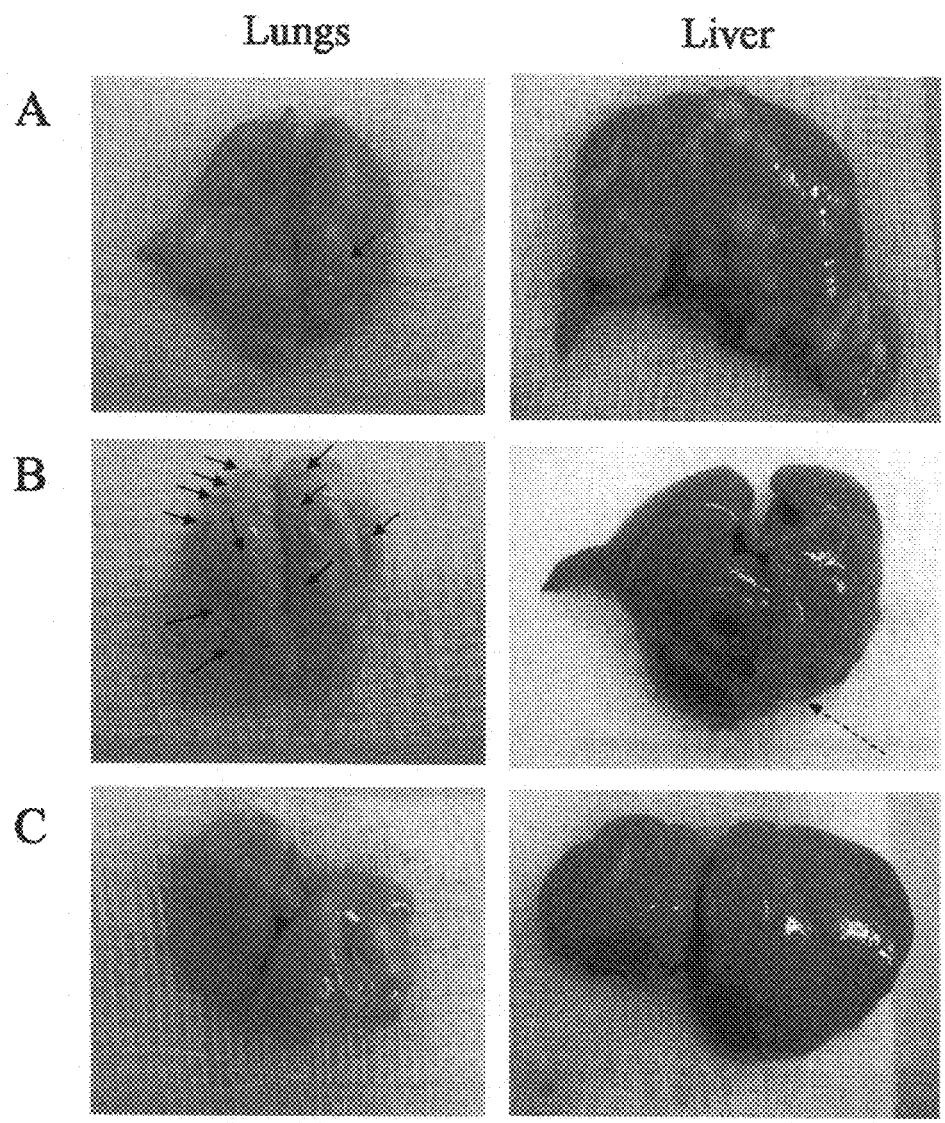
FIG. 18 shows representative examples of intra-hepatic liver cancer recurrence and metastasis and distant lung metastasis induced in the rats of the IR injury group after hepatectomy and ischemia/reperfusion procedures and its protection using the inventive heat stable cross-linked tetrameric hemoglobin.

FIG. 18 shows representative examples of intra-hepatic liver cancer recurrence and metastasis and distant lung metastasis induced in the rats of the IR injury group after hepatectomy and ischemia/reperfusion procedures and its protection using the inventive heat stable cross-linked tetrameric hemoglobin. In FIG. 18A, extensive intrahepatic liver cancer recurrence/metastasis is observed in the IR injury group. Distant lung metastasis is also occurred in the same rat (indicated by a solid arrow). In FIG. 18B, intrahepatic liver cancer recurrence/metastasis is observed in another case in the IR injury group (indicated by a dotted arrow). Extensive lung metastasis is observed in the same case (indicated by solid arrows). In contrast, FIG. 18C shows a representative example of protection from intrahepatic liver cancer recurrence/metastasis and distant lung metastasis in the inventive heat stable cross-linked tetrameric hemoglobin treated rat.

Figure 19:
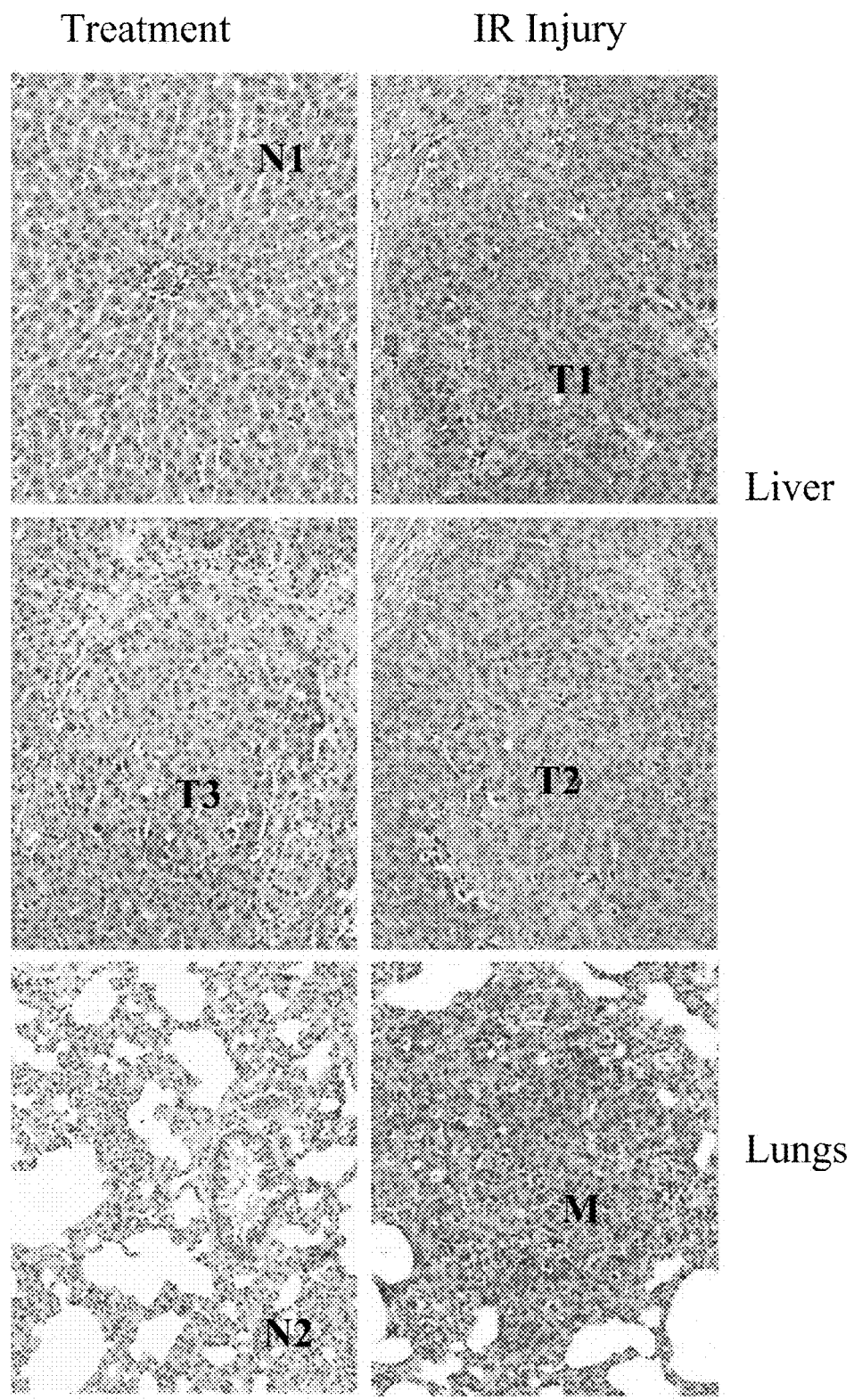
FIG. 19 shows the histological examination in experimental and control groups at four weeks after liver resection and IR injury procedures.

FIG. 19 shows the histological examination in both groups at four weeks after liver resection and IR injury procedures. Histological examination (H&E staining) of liver and lung tissues in both the IR injury and hemoglobin treatment groups is performed to confirm the identity of the tumor nodules. Representative fields showing intrahepatic recurrence/metastasis in the treatment (T3) and IR injury groups (T1 and T2) are shown. Histological examination showing a normal liver architecture in the treatment group is included for comparison (N1). In addition, distant metastasis in the lungs is found in the same rat in IR injury group (M). Lung tissue without metastasis is shown in the treatment group (N2) for comparison.

As a result of the investigation, it is concluded that treatment with the nonpolymeric heat stable cross-linked tetrameric hemoglobin of the present invention has a preventative effect on both the recurrence of hepatic tumors and on metastasis in other organs.

While the foregoing invention has been described with respect to various embodiments, such embodiments are not limiting. Numerous variations and modifications would be understood by those of ordinary skill in the art. Such variations and modifications are considered to be included within the scope of the following claims.

What is claimed is:

1. A method for reducing cancerous hepatic tumor recurrence and minimizing hepatic tumor cell metastasis in a mammal during surgical removal of a hepatic tumor in which the surgical removal of the hepatic tumor includes partial hepatectomy and disruption of blood supply to a region of a mammalian body including the liver comprising:

prior to disrupting blood supply, administering a non-polymeric, highly purified and heat stable oxygen carrier-containing pharmaceutical composition comprising a cross-linked tetrameric hemoglobin with an undetectable dimer concentration to a region of a mammalian body including the liver having a hepatic tumor to be removed;

disrupting blood supply to said region of the body including the liver during at least a portion of the hepatic tumor removal process;

re-establishing blood supply to said region of the body including the liver, the re-establishing of blood supply including further administering the non-polymeric cross-linked tetrameric hemoglobin to said region of the mammalian body including the liver.

2. A method according to claim 1 wherein the cross-linked tetrameric hemoglobin is administered in a range of approximately 0.2 g/kg-1.2 g/kg body weight of the mammal.

3. A method of treating cancerous tissue by administering a non-polymeric, highly-purified and heat stable, oxygen carrier-containing pharmaceutical composition comprising heat-treated, stabilized cross-linked tetrameric hemoglobin having a molecular weight of 60-70 kDa and N-acetyl cysteine at a concentration of 0.2-0.4%, the composition being free of vasoconstricting impurities and protein impurities, non-pyrogenic, endotoxin-free, phospholipid-free, stroma-free, with an undetectable dimer concentration and a methemoglobin level of less than 5%, to a region of a body to a mammal including cancerous tissue be treated by radiation treatment or by chemotherapy treatment, the administration of the oxygen carrier-containing pharmaceutical composition being at a concentration in a range of approximately 0.2-1.2 g/kg body weight at an infusion rate of less than 10 ml/hour/kg body weight at a time prior to radiation treatment or chemotherapy treatment of the cancerous tissue followed by radiation treatment or chemotherapy treatment of the cancerous tissue wherein the cancerous tissue is nasopharyngeal carcinoma or a liver tumor.

4. A method according to claim 3 wherein the cancerous tissue is hypoxic and the administration of the stabilized cross-linked tetrameric hemoglobin increases the oxygenation of the hypoxic cancerous tissue.

5. A method according to claim 3 wherein the cancerous tissue includes a tumor and the treating reduces the size of the tumor.

6. A method according to claim 3 wherein the cancerous tissue receives both radiation treatment and chemotherapy treatment.

7. A method of increasing the oxygenation of hypoxic cancerous tissue in a mammal comprising administering a non-polymeric, highly-purified and heat stable oxygen carrier-containing pharmaceutical composition comprising heat-treated, stabilized cross-linked tetrameric hemoglobin having a molecular weight of 60-70 kDa and N-acetyl cysteine at a concentration of 0.2-0.4%, the composition being free of vasoconstricting impurities and protein impurities, non-pyrogenic, endotoxin-free, phospholipid-free, stroma-free, with an undetectable dimer concentration and a methemoglobin level of less than 5% to a region of a body of a mammal including hypoxic cancerous tissue at a concentration in a range of approximately 0.2-1.2 g/kg body weight at an infusion rate of less than 10 ml/hour/kg body weight, wherein the cancerous tissue is nasopharyngeal carcinoma or a liver tumor.

* * * * *